United States Patent [19]
Tsuchiya

[11] Patent Number: 5,477,051
[45] Date of Patent: Dec. 19, 1995

[54] APPARATUS FOR MEASURING OPTICAL INFORMATION IN SCATTERING MEDIUM AND METHOD THEREFOR

[75] Inventor: Yutaka Tsuchiya, Hamamatsu, Japan

[73] Assignee: Hamamatsu Photonics K.K., Hamamatsu, Japan

[21] Appl. No.: 131,678

[22] Filed: Oct. 5, 1993

[30] Foreign Application Priority Data

Oct. 6, 1992 [JP] Japan .................... 4-267046

[51] Int. Cl.$^6$ .................................. G01J 3/433
[52] U.S. Cl. ................. 250/341.1; 250/339.12; 356/432
[58] Field of Search .................... 250/339.12, 341.1, 250/343; 364/413.01, 413.02, 413.07, 413.08, 413.09, 413.1, 413.11, 413; 328/86, 88; 356/432, 441, 442

[56] References Cited

U.S. PATENT DOCUMENTS

| | | | |
|---|---|---|---|
| 4,407,290 | 10/1983 | Wilber | 128/633 |
| 4,824,242 | 4/1989 | Frich et al. | 356/41 |
| 4,972,331 | 11/1990 | Chance | 364/550 |
| 5,122,974 | 6/1992 | Chance | 364/550 |
| 5,213,105 | 5/1993 | Gratton et al. | 128/664 |

FOREIGN PATENT DOCUMENTS

| | | |
|---|---|---|
| 2254145 | 9/1992 | United Kingdom ........ 356/432 |
| 9009003 | 8/1990 | WIPO . |
| 9300045 | 1/1993 | WIPO . |
| 9309423 | 5/1993 | WIPO . |

OTHER PUBLICATIONS

NIR Spectrophotometry, "Non–Invasive Hemoglobin Oxygenation Monitor and Computed Tomography", SPEI, vol., 1431, (1991), pp. 284–293.

Patterson et al, "Applications of Time–Resolved Light Scattering Measurements to Photodynamic Therapy Dosimetry", SPIE, vol. 1203, (1990), pp. 62–75.

Patterson et al, "Time Resolved Reflectance and Transmittance for the Non–Invasive Measurement of Tissue Optical Properties", Applied Sptics, vol. 28, No. 12, Jun. 1989, pp. 2331–2336.

Sevick et al, "Time–Dependent Photon Migration Imaging", SPIE, vol. 1599, (1991), pp. 273–283.

Fishkin et al, "Diffusion of Intensity Modulated Near–Infrared Light in Turbid Media", SPIE, vol. 1432, (1991), pp. 122–135.

Sevick et al, "Quantitation of Time and Frequency–Resolved Optical Spectra for the Determination of Tissue Oxgenation", Analytical Biochemistry, Vo. 195, (1991) pp. 330–351.

*Primary Examiner*—David P. Porta
*Assistant Examiner*—David Vernon Bruce
*Attorney, Agent, or Firm*—Cushman, Darby & Cushman

[57] ABSTRACT

Modulated light from a light source is incident on the surface of a scattering medium, and light passing through this scattering medium is externally detected. Components having a plurality of angular frequencies $\omega_1$ and $\omega_2$ corresponding to photon density waves propagating in the scattering medium are extracted from this detection signal. The extracted signals corresponding to these waves are compared with a signal of original modulated light to be incident on the scattering medium to detect a quantitatively measurable predetermined parameter such as a phase difference at a detection point for each angular frequency. The detected predetermined parameters have a predetermined relationship with absorptive and scattering constituents of the scattering medium. A pair of predetermined parameters are appropriately arithmetically calculated to eliminate the scattering coefficient, so that only the absorption coefficient can be independently calculated. Various pieces of information (including the linear integration value of the absorption coefficient in the scattering medium, the concentration of the specific material in the scattering medium, and the like) associated with absorption and the like in the scattering medium can be obtained in accordance with the calculated absorption coefficient.

19 Claims, 16 Drawing Sheets

LENS — SCATTERING MEDIUM

OPTICAL FIBER

OPTICAL FIBER

APPARATUS FOR MEASURING OPTICAL INFORMATION IN SCATTERING MEDIUM AND METHOD THEREFOR

BACKGROUND OF THE INVENTION

1. Field of the Invention

The present invention relates to absolute-value measurement of optical information associated with scattering and absorptive constituents in a scattering medium by utilizing modulated light and, more particularly, to an apparatus for measuring optical information in the scattering medium, capable of measuring an equivalent scattering coefficient, an absorption coefficient, and the concentration of a specific constituent in the scattering medium, their time rate changes, spatial distributions, and the like, and improving measurement precision, and a method therefor.

2. Related Background Art

Light does not propagate straight in a scattering medium because the light is scattered and absorbed at random. The total amount of light is not reduced in a scattering medium whose absorption is zero. However, light propagates in the medium at random in a zig-zag manner because the light is scattered by the scattering constituent at random. In this case, an average optical pathlength through which light propagates without the influence of scattering is a reciprocal number of an equivalent scattering coefficient (to be described later). This reciprocal number is called a mean free path or mean diffusion length. This pathlength in a biological sample is about 2 mm. However, as an absorptive constituent is contained in addition to the scattering constituent in a scattering medium, random absorption occurs to attenuate light in accordance with the light propagation path length.

A well-known Lambert-Beer law is valid in the above scattering medium. According to this law, the absorbance or optical density of the scattering medium is proportional to the product of the molar absorption coefficients and the molar concentrations of the constituents and thickness of the scattering medium. This law is regarded as a basic principle in absorbance analysis.

In the absorbance measuring method, the attenuation coefficient by its definition is a sum of an equivalent scattering coefficient and an absorption coefficient. These scattering and absorption coefficients are processed as equivalent parameters. For this reason, it is impossible to separate influences of scattering and absorption and to accurately measure the influence of absorption, e.g., the absorption coefficient. To overcome this, the principle of two-wavelength spectroscopy is generally applied to this absorbance measuring method. More specifically, at least two appropriate light beams having different wavelengths and different absorption coefficients with respect to an absorptive constituent are used to measure the absorbance values.

In this case, it is assumed that the scattering coefficients or equivalent scattering coefficients at these at least two wavelengths are identical to each other or have a very small difference, if any. The influence of scattering is eliminated in accordance with the difference between the absorbance values derived from these at least two light beams, thereby obtaining the absorption coefficient or the concentration of the absorptive constituent.

According to this method, as can be apparent from the above measurement principle, a large error occurs due to the assumption that the scattering coefficients are equal to each other with respect to the light components having different wavelengths. In addition, the influence of scattering, i.e., the scattering coefficient itself cannot be measured. As techniques similar to this, a method of measuring an absorbance difference using two- or three-wavelength continuous, pulsed, or modulated light and a method using the above principle of two-wavelength spectroscopy in addition to the above method of measuring the absorbance difference are also available. These methods also have the same disadvantage as that of the above principle, and this disadvantage cannot be eliminated.

Strong demand has conventionally arisen for measurements of absorptive constituents in scattering media such as living bodies or improvements of measurement accuracy, and various efforts and attempts have been made. Major efforts and attempts are summarized as references[1]–[7] at the end of this section.

In these references, a common problem, i.e., a problem encountered upon application of the principle of two-wavelength spectroscopy to absorbance measurements including scattering, is posed. In addition, the following problems are also posed. In the following description, *) represents the reference number.

Tamura et al.[1] proposed the measuring principle of an oxyhemoglobin concentration and a reduced or deoxygenated hemoglobin concentration in accordance with a change of absorbance optical density with respect to incident light components having three different wavelengths. Optical CT construction using this principle is also attempted. However, this method has the above problem and poses another problem in which a measurement error is increased by the way of handling an optical pathlength upon a change in absorption coefficient in absorbance measurement.

References[2–4] are attempts for time-resolved measurement where time-resolved output signal with respect to the incidence of pulsed light is used to measure internal absorption information. At this time, an output light signal upon incidence of the pulsed light on a scattering medium is a light signal output which has a wide time width caused by scattering and absorption and a long, gradually attenuated tail.

Patterson et al.[2] assumed a model of a uniform scattering medium to analytically obtain a light signal output in response to pulsed light incidence. A waveform representing a time change in intensity of the optical signal given by the formula defined by Patterson et al. matches a waveform obtained by an experiment using a uniform scattering medium. According to them, the absorption coefficient of an absorptive constituent constituting the scattering medium is given by a slope (differential value) obtained when the optical signal is sufficiently attenuated, i.e., when a sufficiently long period elapses.

According to this method, however, since the optical signal corresponding to a portion subjected to absorption coefficient measurement must be sufficiently attenuated, the S/N ratio of the signal becomes low, and an error increases. It is difficult to use this method in practice. In addition, a long period of time must elapse until the optical signal output is sufficiently attenuated, and the measurement time is inevitably prolonged.

To the contrary, Chance et al.[3] proposed a method[3] of obtaining a slope at an earlier timing (when the light intensity is not sufficiently attenuated) to approximate an absorption coefficient with the slope value. According to their report, an error in a simple scattering medium such as a uniform medium is about 10%. However, there is no guarantee that the above waveform is monotonously attenuated in an actual living body having a complicated structure, and an error caused by an increase in DC light component is further added. In the above three references, the scattering coefficient cannot be measured.

Sevick, Chance, et al[4] calculated an average optical pathlength of detected output light components from the barycenter, i.e., the average delay time of the waveform of an output signal obtained by Patterson et al. mentioned above, and confirmed dependency of the average optical pathlength on the absorption coefficient. They also attempted to measure an absorptive constituent localized inside the scattering medium from a change in average optical pathlength[4].

The method of Sevick, Chance, et al. explicitly suggests that application of the concept of the average optical pathlength which depends on absorption allows measurement of absorption information in the scattering medium. However, the above average delay time can be obtained only after the output signal waveform becomes apparent as a whole. For this reason, measurement of the average delay time must be delayed until the output light signal having a long, gradually attenuated tail is sufficiently attenuated, thereby prolonging the measurement time.

According to this method, since the output light signal is obtained by time-resolved measurement, the improvement of measurement precision of time to improve measurement precision of the average optical pathlength undesirably causes a decrease in S/N ratio. Therefore, the measurement precision has a limitation. Signal processing for obtaining the barycenter is complicated, and an apparatus for performing time-resolved measurement is generally complicated and bulky, resulting in an impractical application.

On the other hand, Gratton et al. proposed a method[5] utilizing light modulated with a sinusoidal wave in imaging of the interior of a scattering medium. This method utilizes coherent propagation of a photon density wave having a modulated frequency component in the scattering medium, as will be described in detail with reference to the operational principle of the present invention.

According to their report[5], although a coherent photon density wave propagating in the scattering medium is confirmed in their experiment, optical parameters of a sample actually used in the experiment do not match the theoretically calculated values. This study is still in the stage of fundamental study. No detailed findings and means have been obtained for a method of calculating absorption and scattering coefficients as one of the objects of the present invention, a method of obtaining the concentration of a specific constituent, and the like.

Chance proposed a method and apparatus for determining the concentration of an absorptive constituent in a scattering medium utilizing modulated light in 1989 prior to the report of Gratton et al., and U.S. Pat. No. 4,972,331[6] of this method was issued to Chance in 1990. According to the basic principle of this patent, an output signal upon incidence of modulated light on the scattering medium is detected and compared with a reference waveform (incident light waveform) to determine a quantitatively measurable parameter, an optical pathlength obtained in the time-resolved measurement mentioned earlier is calculated, and the concentration of the absorptive constituent is quantitatively measured.

This patent also discloses an application of the two-wavelength spectroscopy principle. This reference, however, uses two wavelengths to eliminate the influence of scattering. That is, Chance's patent proposes a technique for accurately measuring the optical pathlengths in accordance with a phase difference method. The Chance's patent is substantially identical to the conventional techniques described above and cannot eliminate the conventional drawback. That is, a scattering coefficient and a measurement error caused by a scattering coefficient difference in an application of the two-wavelength spectroscopy cannot be measured.

In addition, Chance also mentions that the phase difference obtained by the method of this patent is equal to the optical pathlength (barycenter of the wave) obtained in the time-resolved measurement and that logarithmic conversion of this phase difference is proportional to the concentration of the absorptive constituent of a scattering medium. The latter fact, however, is greatly different from the analytic and experimental results of the present invention, as will be described in detail later. The present invention does not require the determination of the optical pathlength. That is, the optical pathlength need not be calculated or measured.

In recent years, Sevick, Chance, et al.[7] systematically examined and analyzed the relationship between various parameters obtained in the time-resolved measurement method and a method (they call this method a frequency-resolved measurement method) utilizing the modulated light, including the analysis results of researchers except for Sevick, Chance, et al., and conducted experiments to verify their analysis results[7]. Most of the major conventional methods for measuring absorption information in a scattering medium are examined in this report, which is very convenient for us. The relationship between the parameters obtained by the time-resolved and frequency-resolved measurement methods is clarified. For example, when the modulation frequency is low, the phase difference obtained by the frequency-resolved measurement method is found to be proportional to the average optical pathlength obtained by the time-resolved measurement method. This is partially disclosed in the Chance's patent described above.

The report by Sevick, Chance, et al. describes detailed applications of the time-resolved measurement method which they have been studying. For example, the following method is described in detail. That is, parameters such as an average optical pathlength and an absorption coefficient are obtained from an output light signal obtained by the time-resolved measurement method. By using these parameters, the concentration and absorption coefficient of the absorptive constituent, the degree of saturation of hemoglobin (concentration of oxyhemoglobin with respect to the total amount of oxyhemoglobin and reduced hemoglobin), and the like in the scattering medium are obtained. These measurements employ the above-mentioned principle of two-wavelength spectroscopy, resulting in errors caused by the scattering coefficient differences. As described above, there are no new findings in this report, but this report can serve as a reference for understanding their idea.

Finally, to clarify the foundation of the present invention, differences between the present invention and the Chance's patent[6] "Phase Modulated Spectroscopy" will be briefly described below. It is pointed out that, in the Chance's patent, although two-wavelength spectroscopy has various advantages in detection of changes in hemoglobin and cytochrome in a living tissue, as described in the part of the "background of the invention", the basic problem of a method of this type lies in that an animal model which allows elimination of hemoglobin to allow direct measurement of cytochrome must be referred to calculate the optical pathlength of a living body as an object to be measured because the optical pathlength is unknown.

It is then stated that a possible application of this method is a clinical study of time-resolved spectroscopy (TRS) using a picosecond optical pulse capable of quantitatively measuring a change in hemoglobin concentration upon determination of the optical pathlength and determining the actual concentrations of hemoglobin and cytochrome. In addition, it is suggested that when this time-resolved spectroscopy and continuous wave spectroscopy (CWS) are used together, the optical pathlength of photon migration can be calibrated to widen the application field according to Chance's patent. The above descriptions are assumed to indicate the importance of Chance's patent.

In contrast to a measurement algorithm closely associated with the above optical pathlength, the present invention utilizes a new measurement algorithm using a function having a form excluding the optical pathlength or a form excluding the optical pathlength as a variable. The optical pathlength naturally need not be calculated. In Chance's patent, the difference between the scattering coefficients with respect to different wavelengths causes a measurement error. To the contrary, according to the present invention, the influence of scattering can be eliminated because waves having at least two different frequency components are used in calculating optical information associated with absorption. The optical information associated with absorption can be accurately measured. That is, by using the waves having two different frequencies, the influence of scattering can be perfectly eliminated according to the present invention.

The first part of the "summary of the invention" of the specification of the Chance's patent describes that "when the carrier frequency is selected so that its time characteristics match the delay time of the photon migration during the period between the input to the scattering medium and the output therefrom, it is found that the principle of two-wavelength spectroscopy can be applied to time-resolved spectroscopic measurement". According to a description in the second half of the description of the third embodiment, since a carrier wave having a high frequency of 220 MHz is used in the apparatus of Chance's invention, measurement accuracy of the photon migration time between the input and the output of the characteristic time measured to be about 5 ns can be greatly improved.

The sensitivity of the disclosed apparatus is indicated to be about 70°/ns and 3°/cm of the change in optical pathlength. To apply the principle of two-wavelength spectroscopic measurement to the time-resolved spectroscopic measurement, the value of the carrier frequency must be selected such that the time characteristics of the carrier wave match the delay time between the input and output in photon migration.

According to a description in the second half of the last paragraph in the part of the detailed description, as the great advantage of the phase modulated spectroscopy, i.e., the method of his patent, it is emphasized that the optical pathlength can be obtained without any assumption. According to this description, when the optical output is exponentially attenuated and the photon migration length is large, the phase modulated spectroscopy can provide a function of emphasizing the delay time of about 5 ns, and his method is one of the most convenient embodiments of the time-resolved spectroscopic measurement.

Judging from the above description, Chance's patent is based on the findings obtained in the time-resolved spectroscopic measurement. The optical pathlength is determined by the phase modulated spectroscopy. At this time, the time characteristic, i.e., the period of the carrier wave is set almost equal to the delay time of photon migration, thereby apparently improving measurement accuracy of the delay time, i.e., the optical pathlength.

In other words, in the Chance's patent, a method of applying the principle of two-wavelength spectroscopic measurement to the time-resolved spectroscopic measurement is very effective. However, since determination or measurement of the optical pathlength by the time-resolved spectroscopic measurement is greatly limited due to the time resolution as the performance of the apparatus, complexity of the apparatus, high cost, and the like, the optical pathlength is measured by a simple phase difference method.

To the contrary, as described above, the present invention is based on a measurement method based on the entirely new concept and principle which are different from a conventional time-resolved spectroscopic measurement including the one disclosed in the Chance's patent or the combination of the time-resolved spectroscopic measurement and the two-wavelength spectroscopic measurement.

The optical pathlength measured in Chance's patent need not be measured in the present invention because the present invention is not based on the principle of time-resolved spectroscopic measurement. The present invention does not require selection of the frequency of a carrier wave required in the Chance's patent (according to the present invention, the carrier wave is expressed as a predetermined frequency component constituting modulated light), i.e., the present invention need not satisfy the condition that "the carrier frequency is selected so that its time characteristics match the delay time of the photon migration during the period between the input to the scattering medium and the output therefrom".

The present invention does not have any limitation concerning frequencies in principle. The principle of two-wavelength spectroscopic measurement can be applied in the entire frequency range. In this case, the difference between the scattering coefficients for different wavelengths need not be considered. That is, the present invention uses photon density waves having at least two different frequencies to eliminate the influence of scattering, as compared with the Chance's patent using two different wavelengths.

The differences between the present invention and the prior art have been clarified, and the inventive step, effectiveness, and importance of the present invention will be readily understood.

REFERENCES

1) I. Oda, Y. Ito, H. Eda, T. Tamura, T. Takada, R. Abumi, K. Nagai, H. Nakagawa, and M. Tamura: Non-invasive hemoglobin oxygenation monitor and computed tomography by NIR spectrophotometry, Proc. SPIE, Vol. 1431, pp. 284– 293 (1991)

2) M. S. Patterson, J. D. Moulton, B. C. Wilson, and B. Chance: Application of time-resolved light scattering measurements to photodynamic theraphy dosimetry, Proc. SPIE, Vol. 1203, pp. 62–75 (1990)

3) M. S. Patterson, B. Chance, and B. C. Wilson: Time resolved reflectance and transmittance for the non-invasive measurement of tissue optical properties, Applied Optics, Vol. 28, No. 12, pp. 2331–2336 (1989)

4) E. M. Sevick, N. G. Wang, and B. Chance: Time-dependent photon imaging, Proc. SPIE, Vol 1599, pp. 273–283 (1991)

5) J. Fishkin, E. Gratton, M. J. vande Ven, and W. W. Mantulin: Diffusion of intensity modulated near-infrared light in turbid media, Proc. SPIE, Vol. 1431, pp. 122– 135 (1991)

6) U.S. Pat. No. 4,972,331 (the corresponding Japanese patent is Japanese Patent Laid-Open No. 2-234048)

7) E. M. Sevick, B. Chance, J. Leigh, S. Nioka, and M. Maris: Quantitation of time and frequency-resolved optical spectra for determination of tissue oxygenation, Anal. Biochem., Vol. 195, pp. 330–351 (1991)

SUMMARY OF THE INVENTION

In order to solve the above problems, an apparatus for measuring optical information in a scattering medium comprises (a) light-emitting means for emitting modulated light of a predetermined wavelength, (b) light-incident means for causing the modulated light of the predetermined wavelength to be incident on the scattering medium, (c) photodetecting means for photodetecting the modulated light, changed during propagation in the scattering medium, through an aperture located near an outer surface of the scattering medium, (d) signal extracting means for extracting a signal of a predetermined frequency component constituting the modulated light from signals photodetected by the photodetecting means, (e) parameter detecting means for comparing the signal extracted by the signal extracting means with the signal of the predetermined frequency component of the modulated light to be incident on the scattering medium and detecting a predetermined parameter associated with propagation of a photon density wave having the predetermined frequency component in the scattering medium and scattering and absorption of the light of the predetermined wavelength constituting the photon density wave having the predetermined frequency component in the scattering medium, and (f) arithmetic processing means for calculating optical information associated with the absorption of the scattering medium in accordance with a given relationship between the plurality of predetermined parameters respectively corresponding to signals having at least two predetermined frequency components, and the scattering and absorption for the light of the predetermined wavelength during propagating of the photon density wave having the predetermined frequency component in the scattering medium, using a relationship obtained by eliminating an influence of scattering from the given relationship.

According to the present invention, a method of measuring optical information in a scattering medium comprises (a) the first step of emitting modulated light of a predetermined wavelength, (b) the second step of causing the modulated light of the predetermined wavelength to be incident on the scattering medium, (c) the third step of photodetecting the modulated light, changed during propagation in the scattering medium, through an aperture located near an outer surface of the scattering medium, (d) the fourth step of extracting a signal of a predetermined frequency component constituting the modulated light from signals photodetected in the third step, (e) the fifth step of comparing the signal extracted in the fourth step with the signal of the predetermined frequency component of the modulated light to be incident on the scattering medium and detecting a predetermined parameter associated with propagation of a photon density wave having the predetermined frequency component in the scattering medium and scattering and absorption of the light of the predetermined wavelength constituting the photon density wave having the predetermined frequency component in the scattering medium, and (f) the sixth step of calculating optical information associated with the absorption of the scattering medium in accordance with a given relationship between the plurality of predetermined parameters respectively corresponding to signals having at least two predetermined frequency components, and the scattering and absorption for the light of the predetermined wavelength during propagating of the photon density wave having the predetermined frequency component in the scattering medium, using a relationship obtained by eliminating an influence of scattering from the given relationship.

According to the apparatus for measuring optical information of a scattering medium and a method therefor of the present invention, when modulated light is incident on the scattering medium, the photon density wave having the predetermined frequency component constituting the modulated light is attenuated. Assuming that the modulated light coherently and regularly propagates the scattering medium, a plurality of quantitatively measurable parameters respectively corresponding to the waves having at least two different predetermined frequency components modified by the scattering and absorptive constituents in the scattering medium are arithmetically processed.

That is, a relationship from which the influence of scattering is eliminated using the given relationship between the plurality of parameters and the scattering and absorption of the scattering medium can be derived, and optical information associated with the absorption is calculated from the resultant relationship using the plurality of parameters. Optical information associated with scattering can also be calculated, as needed.

The apparatus and method of the present invention will be described in more detail. In the apparatus and method of the present invention, a signal of output light is optically detected by a photodetector or the like having an aperture located on a side opposite to a modulated light source located near the surface of, e.g., a scattering medium. The signal having the predetermined frequency component is extracted from the output light signal to detect the photon density wave propagating through the scattering medium. The signal extracted as a component corresponding to this photon density wave is compared with the signal of the predetermined frequency component of the originally incident modulated light to detect a quantitatively measurable predetermined parameter such as a phase difference (or a phase delay) $\Phi$ or an amplitude $I_p$ of the photon density wave at the detection point.

This predetermined parameter has a predetermined relationship with an equivalent scattering coefficient $\mu_s'$ of the scattering constituent and an absorption coefficient $\mu_a$ of the absorptive constituent of the scattering medium. For this reason, when a plurality of predetermined parameters obtained for waves having two or more different predetermined frequency components are arithmetically processed on the basis of a finding (e.g., a relation from which the influence of scattering is eliminated) disclosed by the present invention for the first time, various pieces of optical information (including the absorption coefficient, its linear integration value, and the concentration of a specific constituent) associated with absorption in the scattering medium can be obtained from the processed parameters. In addition, optical information (including an equivalent scattering coefficient of a scanning medium, its linear integration value, and the concentration of a specific constituent) associated with scattering can also be obtained, as needed. In this case, the equivalent scattering coefficient is defined as $\mu_s'=(1-g)\mu_s$ where g is the average $\cos\Theta$ value with respect to a scattering angle $\Theta$, and $\mu_s$ is a scattering coefficient. The reciprocal number of $\mu_s'$ is equal to the mean free path of light in the scattering medium.

The predetermined parameter described above is exemplified as the phase difference $\Phi$. Since the phase difference $\Phi$ serves as a function of the equivalent scattering coefficient $\mu_s'$ and the absorption coefficient $\mu_s$, a predetermined parameter $\Phi_1$ for a photon density wave having a first predetermined frequency component having an angular frequency $\omega_1$ and a parameter $\Phi_2$ for a photon density wave having a second frequency component having an angular frequency $\omega_2$ different from the angular frequency $\omega_1$ are obtained. Using the relationship ($\Phi_1$, $\omega_1$, $\mu_s'$, $\mu_s$) and the relationship ($\Phi_2$, $\omega_2$, $\mu_s'$, $\mu_s$), an absorption coefficient $\mu_a$ as the optical information of the scattering medium is obtained. In the simplest case, for example, when the ratio of $\Phi_1$ to $\Phi_2$, i.e., $\Phi_1/\Phi_2$ is obtained, the influence of the scattering constituent is eliminated to obtain a simple formula or relation. In any case, the signals corresponding to the parameters $\Phi_1$ and $\Phi_2$ are arithmetically processed on the basis of the above relationships to obtain the absorption coefficient $\mu_a$ serving as the optical information associated with absorption. Optical information such as the equivalent scattering coefficient $\mu_s'$ and the concentration of a specific constituent is derived from signal processing using the $\mu_a$ value, as needed.

In an optical information measuring apparatus for a scattering medium, optical information associated with scattering and absorption can be directly calculated without calculating a phase difference and the like as the predetermined parameters.

DESCRIPTION OF THE PREFERRED EMBODIMENT

1. Basic of Measurement of Optical Information in Scattering Medium

Light (preferably, near-infrared rays in a living body or the like) which easily propagates through a living body is modulated with a sinusoidal wave between a kHz and GHz range. The behavior of modulated light in the medium upon incidence of the signal modulated with the sinusoidal wave or light constituting the modulated light can be derived from a photon diffusion theory. In this case, a sinusoidal photon density wave having a modulation angular frequency $\omega$ (frequency $f=\omega/2\pi$) accompanies attenuation in the scattering medium, but coherently and regularly propagates in the scattering medium as a wave. This is theoretically and experimentally confirmed by Gratton et al.[5] and the present inventor. This wave will be called the photon density wave, hereinafter. The present inventor filed a patent application (Japanese Patent Application No. 4-192370) concerning an apparatus for measuring absorption information in a scattering medium and a method therefor. This apparatus and method use an approximated solution of a basic equation associated with the principle of the present invention.

The behavior of each photon constituting the above modulated light or the photon density wave can be calculated by a computer. The behavior of the modulated light constituted by these photons can be analyzed, experimented, and examined in accordance with Monte Carlo calculation. The present inventor has made these analyses, experiments, and examinations in Monte Carlo calculation and experiments using standard samples to clarify the behavior of the modulated light or the photon density wave in the scattering medium, a method of quantitatively measuring a specific constituent in a scattering medium, and a method of imaging the modulated light and the specific constituent.

The principle of basic operation of the present invention is clarified for the first time according to the above-mentioned analyses and experiments and will be described below.

Figure 1:
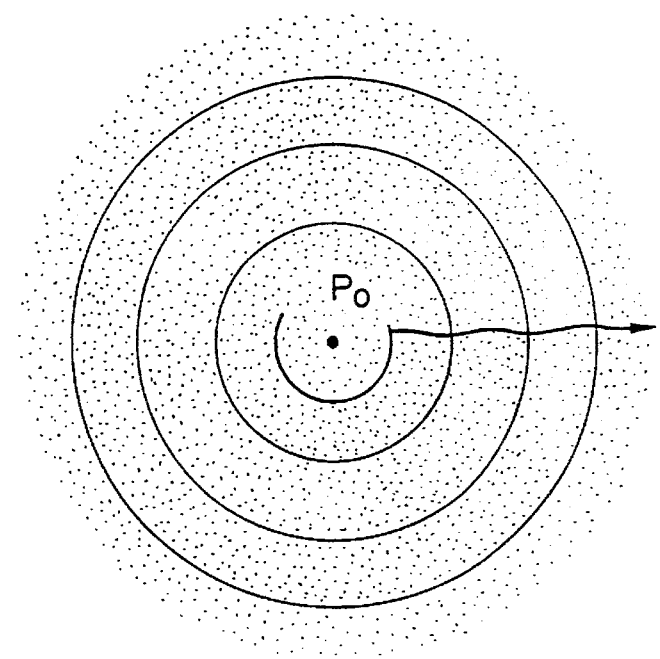
FIG. 1 is a view showing a state in which modulated light emitted from a point light source propagates in an infinite scattering medium as a wave of photon density.

A photon diffusion equation is generally solved under the assumption that a point light source is located inside an infinitely spread scattering medium, as shown in FIG. 1. In this case, the photon density wave of the modulated frequency component ($f=\omega/2\pi$) coherently propagates in the scattering medium, and the wave front of the photon density wave is concentrically spherical.

Figure 2:
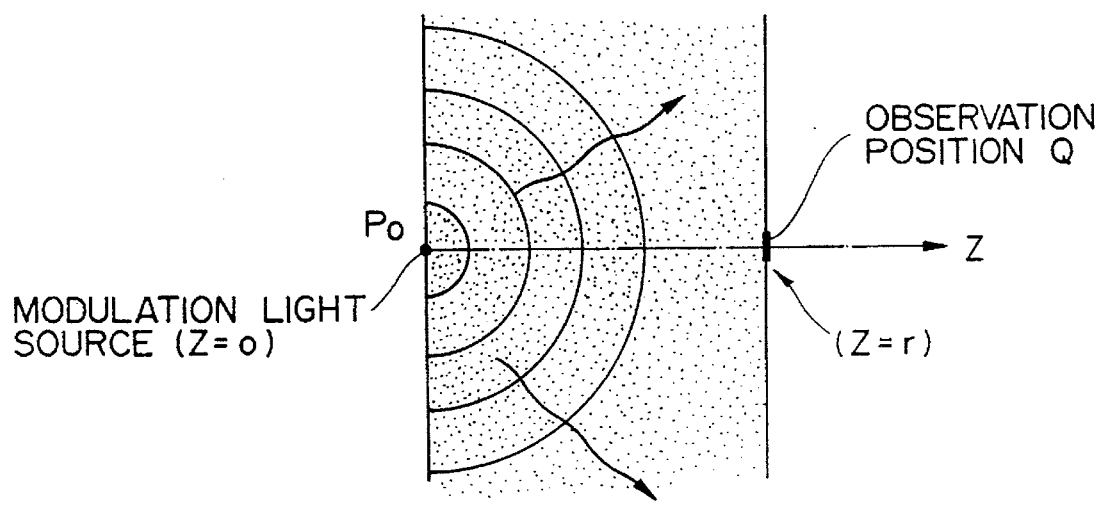
FIG. 2 is a view showing a scattering medium having a finite thickness and a photon density wave generated by a point light source located on the surface of the scattering medium.

To the contrary, in a practical apparatus, modulated light is incident on the outer surface of a scattering medium as in an imaging apparatus for measuring optical information (e.g., a scattering coefficient and an absorption coefficient) as one object of the present invention. In this case, the photon diffusion equation must satisfy the boundary condition on the surface of the scattering medium. This boundary condition is not to cause light or photon diffusion on the outer side of the scattering medium. FIG. 2 shows a state in which modulated light incident from a given point light source onto a slab-like scattering medium propagates in the scattering medium. In this case, at a location except for a location near the surface of the scattering medium, the photon density wave of the predetermined frequency component is regarded to coherently propagate like an almost spherical wave. Therefore, as in FIG. 2, the concentrically spherical photon density wave is regarded to propagate at a location except for the location near the surface of the scattering medium on the light source side. Such a spherical photon density wave is assumed in the following description.

Figure 3:
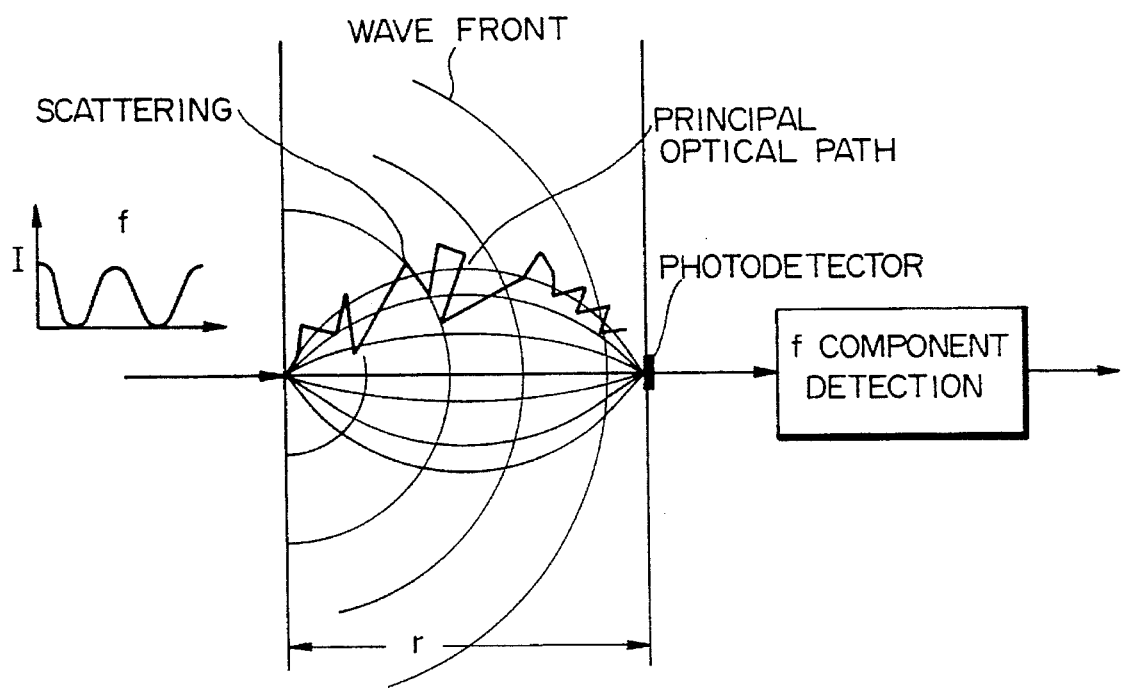
FIG. 3 is a view showing a behavier of the photon density wave and photons constituting the wave in a scattering medium.

FIG. 3 shows a state in which spot-like modulated light is incident on the surface of the scattering medium, photons propagating through the scattering medium are detected by a photodetector practically having a certain input aperture, and a predetermined frequency component signal is extracted from an output signal from the photodetector. In this case, of all the photons detected by the photodetector, photons constituting the photon density wave of the predetermined frequency component are regarded to roughly propagate along the spindle-shaped principal optical path shown in FIG. 3. Reference symbol r in FIG. 3 denotes a distance from the light source to the photodetector (strictly speaking, the position at which light to be detected emerges from the scattering medium). The information detected utilizing the above wave involves the scattering and absorption coefficients of the spindle-shaped portion between the light incident point and the photodetection point.

The above description has already been confirmed by Monte Carlo calculation and experiments using actual samples both by the present inventor. Modulated light of any waveform can be used to apply the above theory if it contains a predetermined frequency component of interest. For example, repeated pulsed light has wave components having the same frequency as the repetition frequency and frequencies which are integer multiples of the repetition frequency. The above theory is applied to any one of the above frequency wave components. The characteristics required for the modulated light are a stable repetition frequency and a stable light intensity.

Even if modulated light is shaped into a broad beam, and the beam is incident on a scattering medium, the above theory can be applied. More specifically, if a wide beam of the modulated light is assumed to be incident on a scattering medium, this is equivalent to a case wherein a large number of point light sources are arranged on the upper surface (regarded as a plane) of a scattering medium. At a paraxial portion of a line connecting the modulated light incident point and the photodetection point, a plane photon density wave of the predetermined frequency component contained in the modulated light is regarded to propagate in the axial direction.

The behavior of the modulated light in the scattering medium is precisely examined on the basis of the above concept, and a relationship between the predetermined parameters used in the present invention and the scattering coefficient of the scattering constituent and the absorption coefficient of the absorptive constituent in the scattering medium to be measured will be described in detail on the basis of an example.

For descriptive convenience, incidence of light modulated with a sinusoidal wave in the form of a spot will be exemplified. The present invention is also applicable to repeated pulsed light and a repeated square photon density wave light and incidence of such light in the form of a parallel beam due to the same reason as described above. For the sake of descriptive simplicity, a solution derived from a photon diffusion equation is approximated in a simple form. However, a result to be obtained can be applied to a case using a more strict solution.

2. Principle of Absorption Coefficient Measurement of Absorptive Constituent in Scattering Medium (1) Description of Propagation of photon density wave Having Predetermined Frequency Component by Photon Diffusion Theory When spot-like light which is modulated with a sinusoidal photon density wave of kHz to GHz is incident on the scattering medium, for example, the behavior of the spot-like light in the medium allows approximation of the following equation from the photon diffusion theory as follows.

Assume that a point light source exists in a uniform scattering medium. A light intensity $I(r,t)$ [photons/sec·mm$^2$] at a position spaced apart from the point light source by a distance r at time t is represented as follows. Note that a modulated photon density wave which propagates through an infinitely spread scattering medium is assumed, but that the modulated photon density wave is also applicable to a scattering medium having a finite size.

$$I(r,t) = (Sv/4\pi\alpha r) \times \{\exp[-r(v\mu_a/\alpha)]^{1/2} + M\exp\{-rA(\omega)\cos B(\omega) - j[rA(\omega)\sin B(\omega) - \omega t + \epsilon]\}\} \quad (1.1)$$

for $$A(\omega) = \{[(v\mu_a)^2 + \omega^2]/\alpha^2\}^{1/4} \quad (1.2)$$
$$B(\omega) = (\tfrac{1}{2})\tan^{-1}(\omega/v\mu_a) \quad (1.3)$$
$$\begin{aligned}D &= \alpha/v \\ &= 1/3\mu_{tr} \\ &= 1/[3(\mu_a + \mu_a')] \\ &= 1/\{3[\mu_a + (1-g)\mu_s]\}\end{aligned} \quad (1.4)$$

where
S: the number of incident photons generated by a light source [photons/sec]
M: the degree of modulation of the modulated light
$\omega$: the angular frequency [rad/sec] of the modulated wave
$\alpha$: the photon diffusion constant [mm$^2$/sec]
$\epsilon$: the fixed phase term
D: the photon diffusion coefficient [mm]
v: the speed [mm/sec] of light in the scattering medium (the speed of light in a vacuum is c=vn where n is the refractive index)
g: the average value of cos$\theta$ with respect to the scattering angle $\theta$
$\mu_{tr}$: the light attenuation coefficient [mm$^{-1}$]
$\mu_a$: the absorption coefficient [mm$^{-1}$]
$\mu_s$: the scattering coefficient [mm$^{-1}$]
$\mu_a'$: the equivalent scattering coefficient [=(1-g)$\mu_s$]

At this time, a component $I_w(r,t)$ whose frequency is expressed as f=$\omega/2\pi$ is represented as follows.

$$I_w(r,t) = (Sv/4\pi\alpha r)M \exp\{-rA(\omega)\cos B(\omega) - j[rA(\omega)\sin B(\omega) - \omega t + \epsilon]\} \quad (1.5)$$

Therefore, a phase difference $\Phi$ and an amplitude $I_p$ of the photon density wave represented by equation (1.5) are approximated as follows.

$$\Phi \approx rA(\omega)\sin B(\omega) \quad (1.6)$$

$$I_p \approx (Sv/4\pi\alpha r)M \exp[-rA(\omega)\cos B(\omega)]$$

That is, $$\ln(SvM/4\pi\alpha r I_p) \approx rA(\omega)\cos B(\omega) \quad (1.7)$$

where ln represents the natural logarithm. These approximations are used to make the following description.

Equations (1.6) and (1.7) can be further simplified as follows.

If $(\omega v\mu_a) = y > 0$, then $$A(\omega) = (v\mu_a/\alpha)^{1/2}(1+y^2)^{1/4}$$

$$\sin B(\omega) = \sin[(1/2)\tan^{-1}y]$$
$$= \{(1/2)[1 - \cos(\tan^{-1}y)]\}^{1/2}$$
$$= \{(1/2)[1 - (1 + y^2)^{-1/2}]\}^{1/2}$$

Therefore, $$\Phi^2 = r^2(v\mu_a/\alpha)(1+y^2)^{1/2} \times$$
$$(1/2)[1 - (1+y^2)^{-1/2}]$$
$$= (r^2/2)(v\mu_a/\alpha)[(1+y^2)^{1/2} - 1]$$
$$\Phi^2 = (r^2/2\alpha)\{[\omega^2 + (v\mu_a)^2]^{1/2} - v\mu_a\}$$

That is, $$\Phi^2 = 3[\mu_a + (1-g)\mu_s](r^2/2v) \times \{[\omega^2 + (v\mu_a)^2]^{1/2} - v\mu_a\} \quad (1.8)$$

Similarly, from equation (1.7), $$[\ln(SvM/4\pi\alpha r I_p)]^2 = 3[\mu_a + (1-g)\mu_s](r^2/2\ v) \times \{[\omega^2 + (v\mu_a)^2]^{1/2} + v\mu_a\} \quad (1.9)$$

Equations (1.8) and (1.9) represent approximated solutions of equation (1.1) for the photon density wave having the angular frequency $\omega$ coherently propagating in the scattering medium. These equations are used as the basic equations of the principle of the present invention. A more strict solution of the photon diffusion equation includes the second term, i.e., a correction term. However, the number of unknown quantities of this correction term is two, i.e., the equivalent scattering coefficient $\mu_s'$ and the absorption coefficient $\mu_a$, and it is not related to the form of the correction term. Therefore, as will be described later, the absorption coefficient $\mu_a$ and the equivalent scattering coefficient $\mu_s'$ can be uniquely determined from two, simultaneous equations, representing measurement values $\Phi_1$ and $\Phi_2$ for the modulation angular frequencies $\omega_1$ and $\omega_2$. Note that the above relation and equations are disclosed for the first time by the present invention.

A living body, a plant tissue, or the like can be one object to be measured of the present invention. In this case, generally, condition $\mu_a << \mu_s' = (1-g)\mu_s$ is satisfied. For example, parameter values for a standard living body are as follows.

$$\mu_a = 0.01 \text{ mm}^{-1}$$
$$\mu_s = 3 \text{ mm}^{-1}$$
$$g = 0.85$$
$$\mu_s' = (1-g)\mu_s = 0.45 \text{ mm}^{-1}$$
$$n = 1.33$$
$$v = 3 \times 10^{11}/1.33 = 2.26 \times 10^{11} \text{ mm/sec}$$
$$v\mu_a = 2.26 \times 10^9 = 2\pi \times 3.6 \times 10^8 \text{ sec}^{-1} \quad (1.10)$$

Since $\mu_a << \mu_s' = (1-g)\mu_s$, the following equation can be obtained from equations (1.8) and (1.9).

$$\Phi^2 = \{[3(1-g)\mu_s r^2]/(2v)\} \times \{[\omega^2 + (v\mu_a)^2]^{1/2} - v\mu_a\} \quad (1.11)$$

$$[\ln(SvM/4\pi\alpha r I_p)]^2 = 3(1-g)\mu_s r^2/2v \times \{[\omega^2 + (v\mu_a)^2]^{1/2} + v\mu_a\} \quad (1.12)$$

Equations (1.11) and (1.12) can be utilized for measuring a scattering medium satisfying condition $\mu_a << \mu_s' = (1-g)\mu_s$.

(2) Calculation of Absorption Coefficient

To obtain the absorption coefficient, waves having two different frequency components (angular frequencies $\omega_1$ and $\omega_2$) are used. In this case, even if the angular frequencies are changed from $\omega_1$ to $\omega_2$ in the same scattering medium while other parameters are kept constant, the scattering and absorption coefficients of the scattering medium remain the same because the light wavelength is constant. When modulated light components having two angular frequencies $\omega_1$ and $\omega_2$ are incident on a scattering medium at a given position and are detected at another given position, r remains the same. It should be noted that a large error occurs due to the difference of scattering coefficients for these two wavelengths.

If the measurement values $\Phi$ of the predetermined parameter corresponding to the detected waves are as follows:

$$\Phi = \Phi_1 \text{ for } \omega = \omega_1$$
$$\Phi = \Phi_2 \text{ for } \omega = \omega_2 \quad (1.13)$$

the following equation is derived from equation (1.8).

$$\Phi_1^2/\Phi_2^2 = \{[\omega_1^2 + (v\mu_a)^2]^{1/2} - (v\mu_a)\} \div \{[\omega_2^2 + (v\mu_a)^2]^{1/2} - (v\mu_a)\} \quad (1.14)$$

In this case, v is known or can be measured or calculated by other methods. For example, water is a major component of the living body. The value v is given by equation (1.10) described above. Substitutions of the known value v, the values of the predetermined $\omega_1$ and $\omega_2$, and the values of $\Phi_1$ and $\Phi_2$ as measurement values into equation (1.14) uniquely yield the absorption coefficient $\mu_a$ of the absorptive constituent of the scattering medium. The calculation of obtaining this $\mu_a$ can be executed using a computer at high speed. Substitutions of the value $\mu_a$ and the value r determined by the measuring system into equation (1.8) yield the equivalent scattering coefficient $\mu_s' = (1-g)\mu_s$.

Since the values $\Phi_1$ and $\Phi_2$ are measurement values, their precision is limited to, e.g., about 0.1° ($1.75 \times 10^{-3}$ rad). As is apparent from equation (1.14), to obtain $\mu_a$ with high accuracy, $\omega_1$ and $\omega_2$ are preferably selected to have almost the same order as that of the $v\mu_a$ value (for example, $\omega_1$ and $\omega_2$ are about $10^8$ to $10^{10}$ because $v\mu_a = 2.26 \times 10^9$ for $v = 2.26 \times 10^{11}$ mm/sec and $\mu_a = 0.01 \times 10^{-3}$ mm$^-$) or $\omega_1$ and $\omega_2$ are preferably selected to satisfy condition $\omega_1 < v\mu_a < \omega_2$ or conversely $\omega_1 > v\mu_a > \omega_2$. In addition, when the number of predetermined frequencies is three or more, an improvement of measurement precision can be expected.

A method of using the ratio $\Phi_1^2/\Phi_2^2$ is exemplified as a practical method of obtaining the absorption coefficient $\mu_a$ based on the relationship between $\Phi_1$ and $\omega_1$ and the relationship between $\Phi_2$ and $\omega_2$. Any form may be used if these relationships are derived from equation (1.8) or an equation representing a more strict solution of the photon diffusion equation, as described above. Since these relationships can be expressed by simultaneous equations including two unknown quantities, the absorption coefficient $\mu_a$ and the equivalent scattering coefficient $\mu_s'$, the two unknown quantities can be uniquely determined. When a simple approximated solution is used for example, $\Phi_1/(\Phi_2, (\Phi_1^2 - \Phi_2^2)/(\Phi_1^2 - \Phi_3^2)$, or the like may be used. In this case, $\Phi_3$ is a phase difference obtained in response to an angular frequency $\omega_3$.

To measure parameters for three different predetermined frequencies, a method of obtaining $(\Phi_1 - \Phi_2)/(\Phi_1 - \Phi_3)$ and then calculating the absorption coefficient $\mu_a$ can be used, although the equation form is slightly complicated. In this case, since $(\Phi_1 - \Phi_2)$ and $(\Phi_1 - \Phi_3)$ are differences between the phase differences, the origin (zero point) of the phase difference $\Phi$ need not be detected and then it facilitates actual measurements.

A similar result can be obtained for the amplitude $I_p$ by considering the logarithm expressed in equation (1.9). In this case, a photon diffusion constant $\alpha$ or a photon diffusion coefficient D must be separately obtained. For example, as can be apparent from equation (1.4), the photon diffusion coefficient D can be obtained by actually measuring an absorption coefficient in absorbance measurement.

As described above, the phase difference $\Phi$ and the amplitude $I_p$ as the predetermined parameters can be equally processed although the forms of equations are different from each other. For the sake of descriptive simplicity, the phase difference $\Phi$ as the predetermined parameter will be exemplified. The phase difference $\Phi$ requires a simpler equation than the amplitude $I_p$.

It should be noted that the influence of the scattering constituent is eliminated from equation (1.14). That is, equation (1.14) indicates that the absorption coefficient of an absorptive constituent in a scattering medium containing a scattering constituent can be measured with high precision. This naturally results from the basic principle of the present invention based on measurement using two different angular frequencies $\omega_1$ and $\omega_2$ in equation (1.8). Therefore, this indicates that the equivalent scattering coefficient $\mu_s'$ and the absorption coefficient $\mu_a$ can be uniquely obtained by the present invention. Various expression forms such as the above-mentioned method of obtaining a more strict solution are available to obtain the absorption coefficient $\mu_a$.

Judging from the above description, the equivalent scattering coefficient and the absorption coefficient of an intralipid solution serving as a standard scattering medium sample whose high-precision measurement is conventionally difficult can be measured. The present invention thus has a very high usefulness. That is, the absorption coefficient and the equivalent scattering coefficient can be accurately measured by the present invention if a scattering medium has scattering and absorption properties.

This new finding of the present invention is utilized in quantitative measurement of the concentration of an absorptive constituent as another object of the present invention. The concentration of a specific constituent is obtained from the absorption coefficient in accordance with the Lambert-Beer law.

The absorption coefficient $\mu_a$ thus obtained is an axial integration value of the absorption coefficient $\mu_a$ of a spindle-shaped portion having the length r along a straight line obtained by connecting a point at which modulated light is incident on the scattering medium and a photodetection point. If this value is regarded as a linear integration value along this straight line, a tomogram associated with the absorption coefficient $\mu_a$ can be obtained using simple imaging and image reconstruction as in X-ray CT. In addition, by similar processing, imaging and reconstruction of a tomogram can be performed for hemoglobin saturation and an absorptive constituent distribution. Imaging and reconstruction of a tomogram can also be performed for the scattering coefficient.

3. Measurement of Absorption Information

As described above, the absorption coefficient is obtained by equation (1.14) and the like. Assume measurements using light components having different wavelengths or measurements at different times and places. The principle of measurement for typical examples will be described below. The detailed arrangements of these measurement apparatuses will be described in detail in the description of preferred embodiments.

(1) Measurement of Concentration of Hemoglobin

Figure 4:
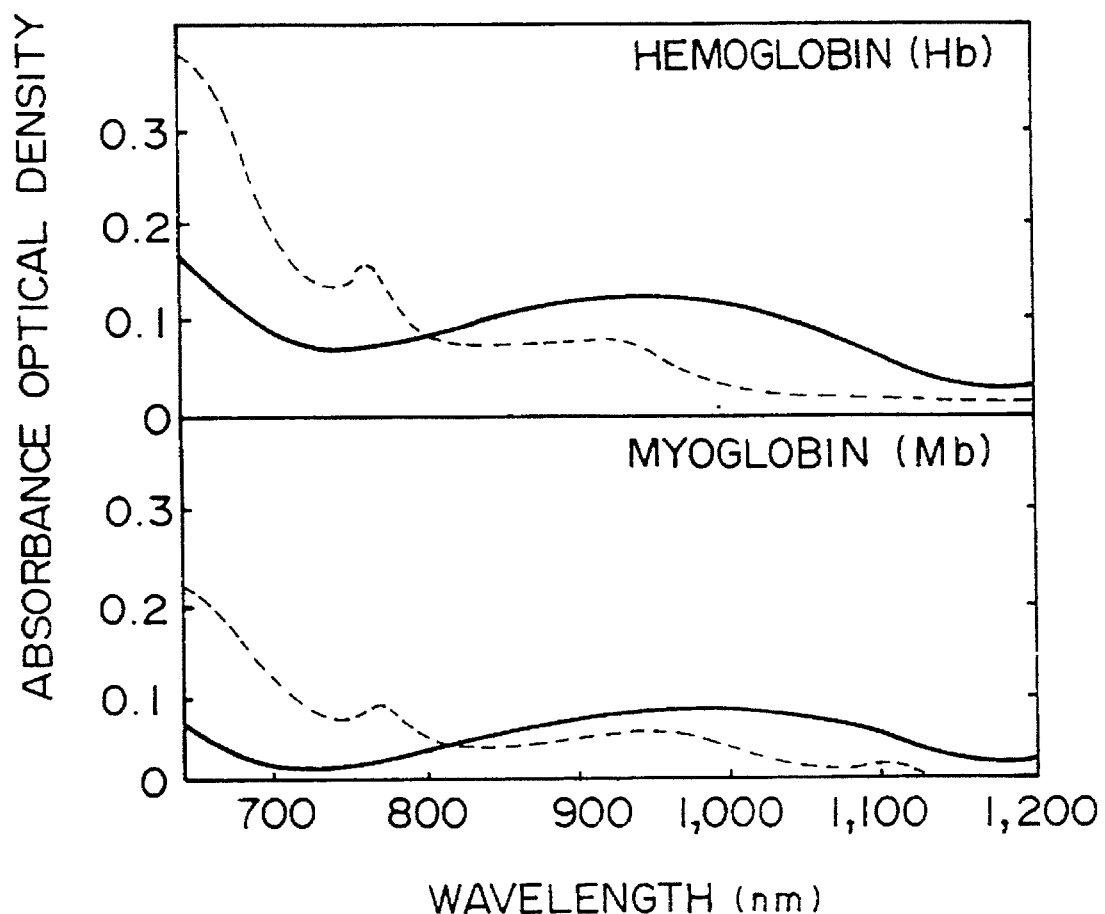
FIG. 4 is a graph showing absorption spectra of various biological materials.

Main absorptive constituents in a mammalian brain are water, cytochrome, oxyhemoglobin, and reduced hemoglobin. Absorption of water and cytochrome in a near-infrared range is negligibly small with respect to oxyhemoglobin and reduced hemoglobin. Oxyhemoglobin and reduced hemoglobin have different absorption spectra, as shown in FIG. 4. The skull is regarded as a scattering medium with respect to near-infrared rays.

If setup is fixed by the method described in the above section, and the absorption coefficients $\mu_{a1}$ and $\mu_{a2}$ are obtained for two modulated light components having wavelengths $\lambda_1$ and $\lambda_2$, respectively, the following equations are established in accordance with the Lambert-Beer law as follows.

$$\mu_{a1} = \epsilon_{Hb,1}[Hb] + \epsilon_{HbO,1}[HbO]$$
$$\mu_{a2} = \epsilon_{Hb,2}[Hb] + \epsilon_{HbO,2}[HbO]$$

where $\epsilon_{Hb,1}$: the molar absorption coefficient $[\text{mm}^{-1} \cdot \text{M}^{-1}]$ of reduced hemoglobin at the wavelength $\lambda_1$ $\epsilon_{HbO,1}$: the molar absorption coefficient $[\text{mm}^{-1} \cdot \text{M}^{-1}]$ of oxyhemoglobin at the wavelength $\lambda_1$ $\epsilon_{Hb,2}$: the molar absorption coefficient $[\text{mm}^{-1} \cdot \text{M}^{-1}]$ of reduced hemoglobin at the wavelength $\lambda_2$ $\epsilon_{HbO,2}$: the molar absorption coefficient $[\text{mm}^{-1} \cdot \text{M}^{-1}]$ of oxyhemoglobin at the wavelength $\lambda_2$

[Hb]: the molar concentration [M] of reduced hemoglobin

[HbO]: the molar concentration [M] of oxyhemoglobin

The molar concentration [Hb] of reduced hemoglobin and the molar concentration [HbO] of oxyhemoglobin can be obtained from the coefficients $\mu_{a1}$ and $\mu_{a2}$ calculated from the measured values, and the known parameters $\epsilon_{Hb,1}$, $\epsilon_{HbO,1}$, $\epsilon_{Hb,2}$, and $\epsilon_{HbO,2}$.

When quantitative measurement of the concentrations of three constituents whose absorption spectra are known in such a case that the cytochrome or the like is taken into consideration, three-wavelength light is used. In quantitative measurement of the concentrations of n constituents whose absorption spectra are known, the measurement values of the absorption coefficients at n wavelengths are generally used to obtain the values in the same manner as described above.

Since the degree Y of saturation is given as follows:

$$Y = [HbO]/([Hb] + [HbO])$$

the following equation is obtained.

$$\mu_{a1}/\mu_{a2} = [\epsilon_{Hb,1} + Y(\epsilon_{HbO,1} - \epsilon_{Hb,1})] + [\epsilon_{Hb,2} + Y(\epsilon_{HbO,2} - \epsilon_{Hb,2})]$$

Y is calculated from the known parameters $\epsilon_{Hb,1}$, $\epsilon_{HbO,1}$, $\epsilon_{Hb,2}$, and $\epsilon_{HbO,2}$ and the coefficients $\mu_{a1}$ and $\mu_{a2}$ calculated from the measured values.

In the above method, absorption coefficients respectively corresponding to the wavelengths of light components are accurately obtained by the method disclosed for the first time by the present invention. The wavelength dependency of the equivalent scattering coefficient which poses a problem in the conventional absorbance measuring method need not be considered, and measurement errors caused by this method can be eliminated. If a wavelength ($\approx 800$ nm, isosbestic wavelength) for obtaining the same absorption level for both oxyhemoglobin and reduced hemoglobin is used, the above equation can be made simpler.

(2) Measurement of Change in the Concentration of Absorptive Constituents over Time When the measurements described above are performed at different times, a change in the concentration of absorptive constituents over time or a change in absorption coefficient over time, a change in concentration of the absorptive constituent over time, a change in saturation over time, a change in equivalent scattering coefficient over time, a change in concentration of the scattering constituent over time, and the like can be measured.

(3) Imaging

The measurement values of the scattering information and the absorption information which are obtained by the above method are regarded as linear integration values of optical information such as the equivalent scattering coefficient, the absorption coefficient, the concentration of the specific constituent, and the degree of saturation in the scattering medium, which are included in the spindle-shaped portion along the straight line obtained by connecting the spot-like modulated light incident position to the photodetection point. When the above measurements are performed at a large number of locations on a relatively thin (i.e., the distance r is small) scattering medium, a two-dimensional distribution measurement, i.e., imaging can be performed. In this case, it is more convenient to use a value normalized with the distance r. The distance r can be easily measured by a conventional distance measuring apparatus. A plurality of photodetectors can also be utilized.

(4) Measurement of Tomogram

Multi-point measurement is performed along a slice of the scattering medium to obtain the above linear integration value of absorption coefficient or the concentration of the specific constituent as in (1). The resultant absorption coefficient or the concentration of the specific constituent is used to obtain a tomogram as in X-ray CT. In this case, the value normalized with the distance r is used. A plurality of photodetectors can also be used.

(5) Arrangement of Measuring Apparatus

Figure 5:
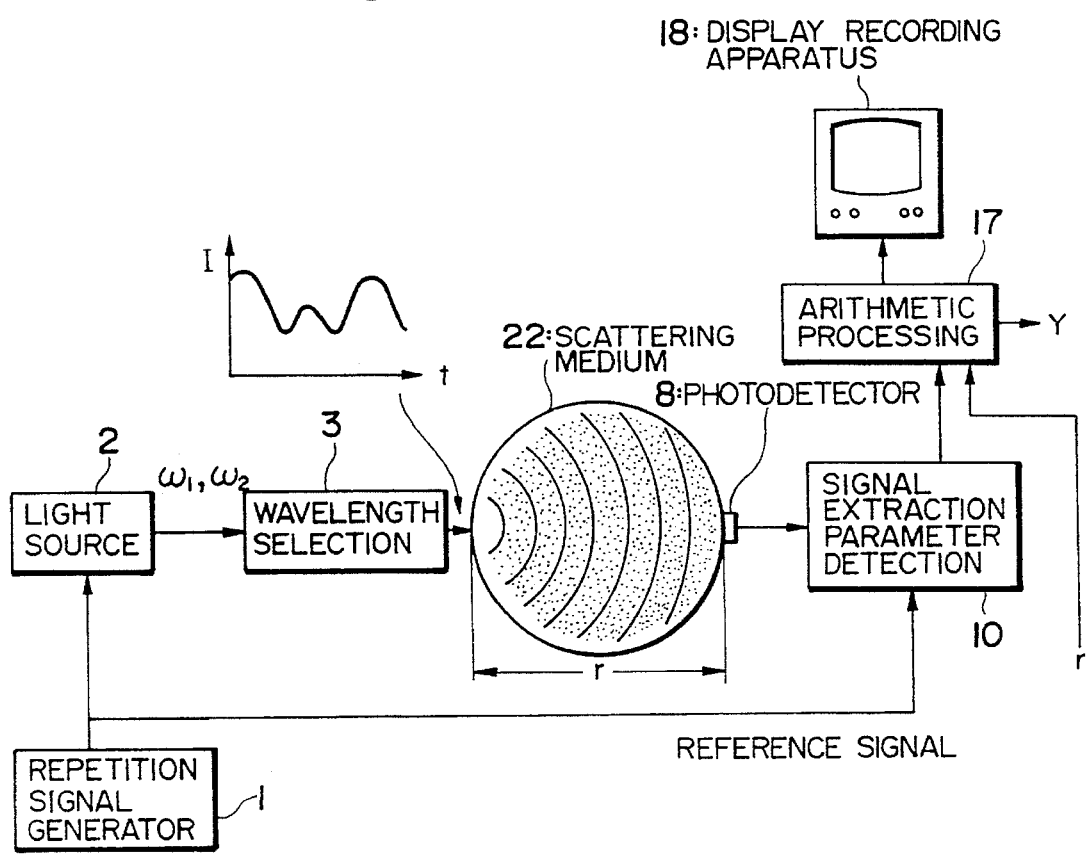
FIG. 5 is a diagram showing an apparatus for measuring optical information in a scattering medium.

FIG. 5 shows a detailed arrangement of a scattering medium optical information measuring apparatus according to the present invention. A light source 2 is driven in accordance with an output signal from a repetition signal generator 1 and generates modulated light having two predetermined angular frequency components $\omega_1$ and $\omega_2$. In this case, this light source can generate a plurality of modulated light components for each of light components having a plurality of different wavelengths. In this case, a method of synthesizing light components having a plurality of different wavelengths from a light source or a method of switching between the light components along the time axis can be used.

A desired wavelength of the modulated light can be selected by a wavelength selecting means 3 such as a spectral band pass filter. The modulated light having the selected wavelength is focused and incident on one point on the surface of a scattering medium 22 serving as an object to be measured. Light propagating in the scattering medium is detected by a photodetector 8 having an aperture at a position (photodetection point) opposite to the modulated light incident point of the scattering medium. A first unit 10 extracts sinusoidal waves respectively corresponding to the two predetermined angular frequency components $\omega_1$ and $\omega_2$ from the signal from the photodetector. These extracted sinusoidal waves are compared with a reference signal (preferably a sinusoidal wave) synchronized with the modulated light. A parameter, e.g., a phase difference, associated with each photon density wave changed during propagation through the scattering medium is obtained. The wavelength of the modulated light incident on the scattering medium is changed to obtain a predetermined parameter in the same manner as described above.

An arithmetic processing means 17 serving as a second unit calculates optical information associated with scattering and absorption on the basis of a plurality of predetermined parameters. More specifically, using the relationship between the phase difference as a predetermined parameter, represented in equation (1.14), and the equivalent scattering and absorption coefficients of the scattering medium, the absorption coefficient and the equivalent scattering coefficient are obtained by operation. A plurality of absorption coefficients are obtained from a plurality of predetermined parameters, i.e., a plurality of phase differences for modulated light components having different wavelengths. Using the resultant values, the concentration of a specific constituent, the degree of hemoglobin saturation, and the like are calculated.

The position of the incident point of the modulated light incident on the scattering medium and the position of the photodetection point are scanned (not shown) to obtain information associated with absorption at each portion of the scattering medium, e.g., the degree of hemoglobin saturation. When the obtained information is stored in a frame memory (not shown) and is read out in accordance with a television scheme, an image representing a distribution of the saturation degree is obtained. A display recording means 18 is used in such data display recording. In this case, the distance r between the modulated light incident point and the photodetection point is measured, and the value normalized with the distance r is used. A tomogram can be reconstructed using this value as in X-ray CT.

The arrangements of the respective components of the scattering medium optical information measuring apparatus will be described below. These components are also used in various embodiments to be described below.

Figure 6:
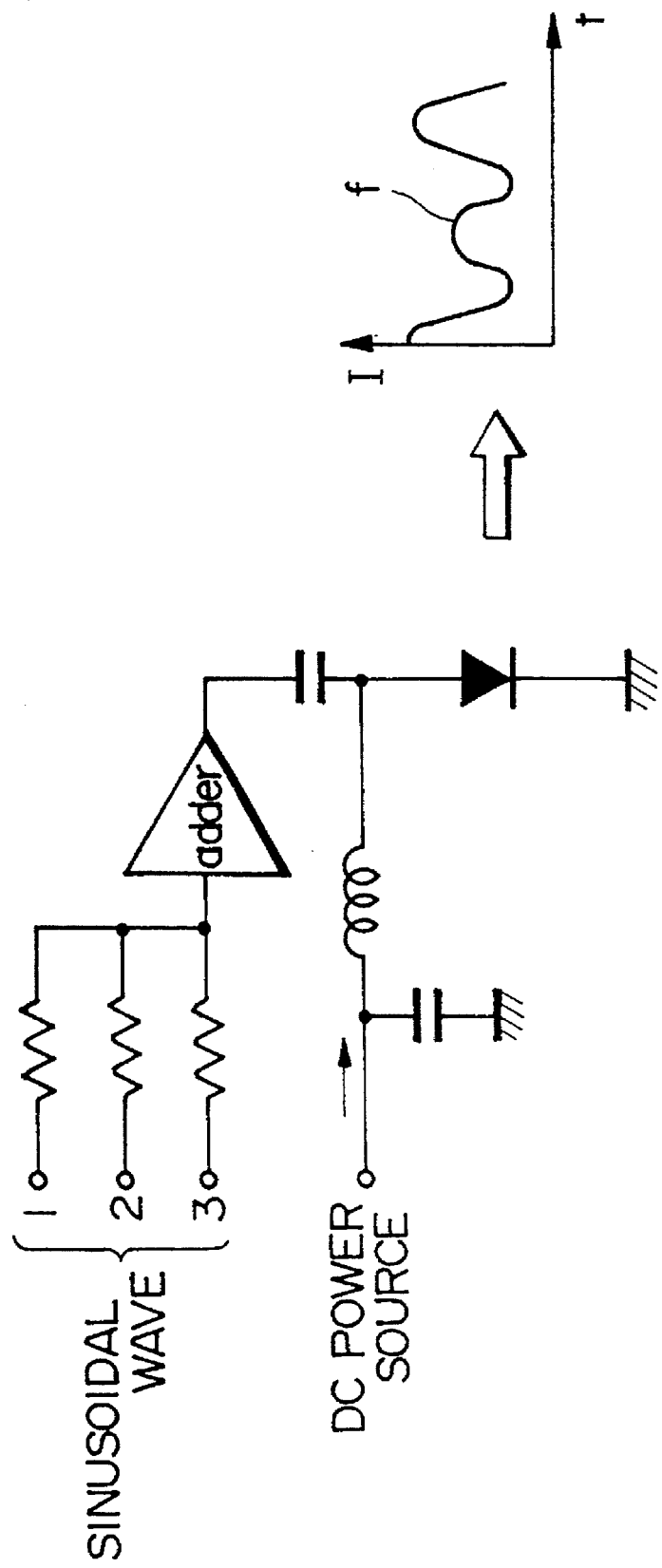
FIG. 6 is a view showing an example of generation of modulated light.

Modulated light containing at least two predetermined frequency components is generated using current modulation of a laser diode, as shown in FIG. 6. In this case, a current used to drive the laser diode is generated by causing an adder to add the two sinusoidal waves having the predetermined frequency components.

Also, as previously described, this light source may generate pulsed light or a square wave. The laser diode can easily generate these modulated light components by current modulation. In addition to this, a method of generating modulated light using beating of a CW laser or an optical modulator is also available. The two different frequency components may be switched along the time axis and may be generated in a time division manner.

The modulated light components having different wavelengths can be generated using a plurality of light sources having different wavelengths. These light components may be simultaneously output or may be switched and output in a coaxial manner using a half mirror. An optical switch may be utilized in wavelength selection. In addition, the coaxial modulated light components having different wavelengths may be selected by a wavelength selection filter at a position immediately before the light incident position or at a position immediately before a photodetector upon direct incidence of these parallel modulated light components on the scattering medium.

Figure 7A:
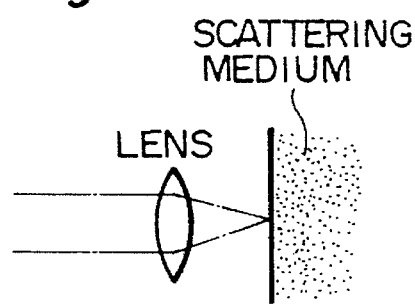
FIGS. 7A to 7D are views showing examples of incidence of modulated light on a scattering medium.
Figure 7B:
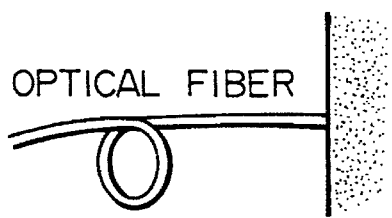
Figure 7C:
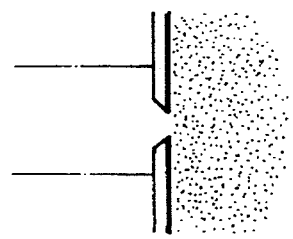
Figure 7D:
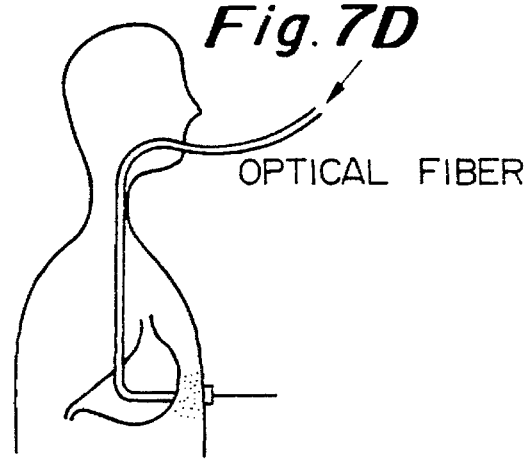

To cause the above-mentioned modulated light to be incident on a scattering medium such as a living body, a method utilizing a condenser lens (FIG. 7A), an optical fiber (FIG. 7B), or a pinhole (FIG. 7C), or a modulated light incident method using a gastrocamera (FIG. 7D) or the like may be used.

Figure 8A:
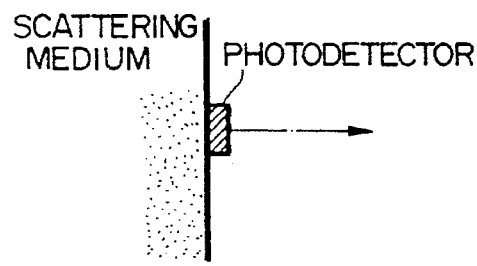
FIGS. 8A to 8D are views showing examples of modulated light detection.
Figure 8B:
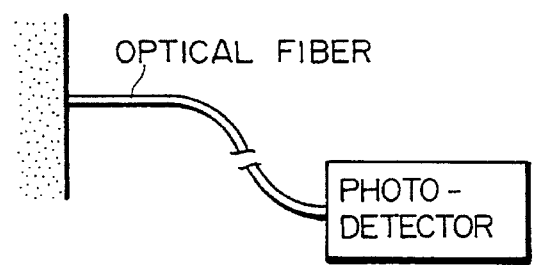
Figure 8C:
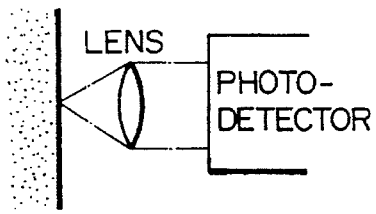
Figure 8D:
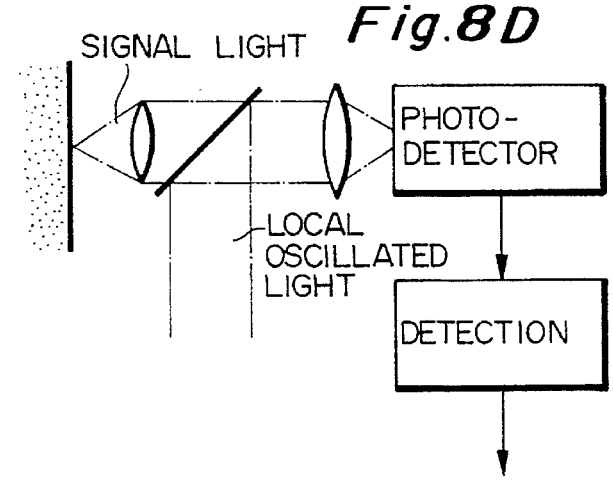

A means for detecting the changed modulated light propagating through the scattering medium may be constituted by direct photodetection (FIG. 8A), a method of detecting the light through an optical fiber and a lens (FIGS. 8B and 8C), a heterodyne detection method of a specific frequency component (FIG. 8D), or the like.

Figure 9A:
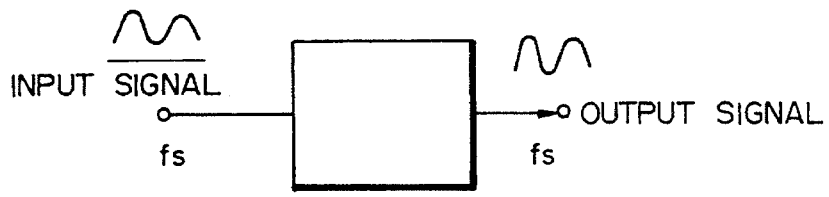
FIGS. 9A to 9C are diagrams showing examples of extracting a specific frequency component signal.
Figure 9B:
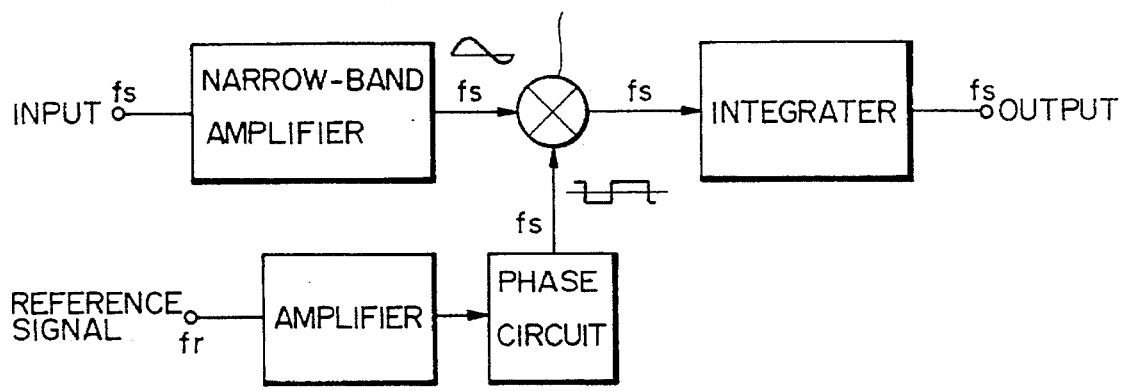

The means for extracting the signal having the specific frequency signal may be constituted by a method using a narrow-band amplifier (FIG. 9A), a method using a lock-in amplifier (FIG. 9B), a heterodyne type lock-in amplifier (FIG. 9C), or the like. A reference signal synchronized with the modulated light is required in the method using the lock-in amplifier. The output signal from the repetition signal generator 1 shown in FIG. 5 is used as this reference signal. When the modulated light contains two predetermined frequency components, an input to the lock-in amplifier is not changed, and only the reference signal is switched, thereby extracting signals having two different predetermined frequency components.

Figure 10A:
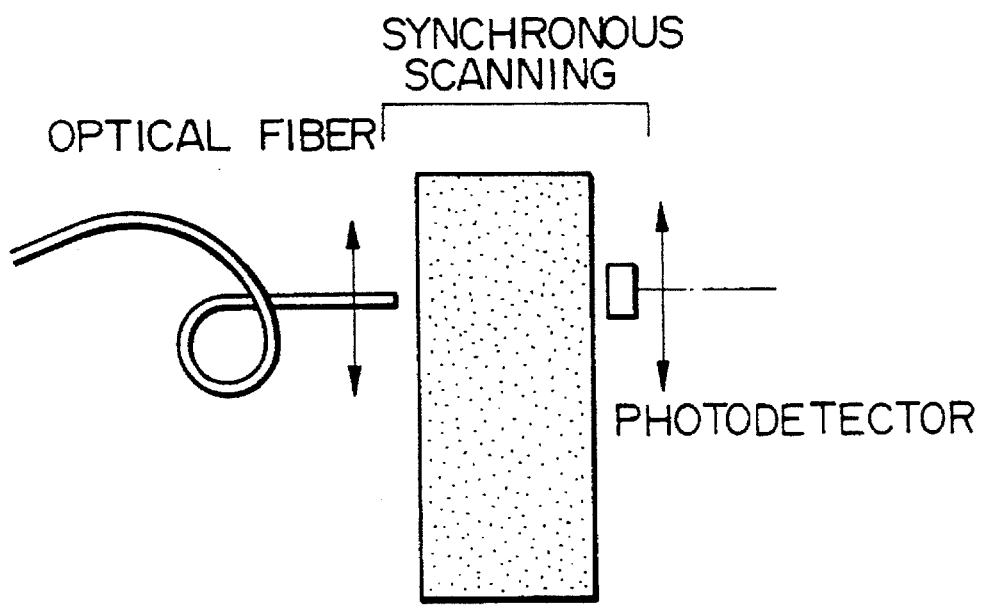
FIGS. 10A and 10B are views showing examples of scanning for imaging.
Figure 10B:
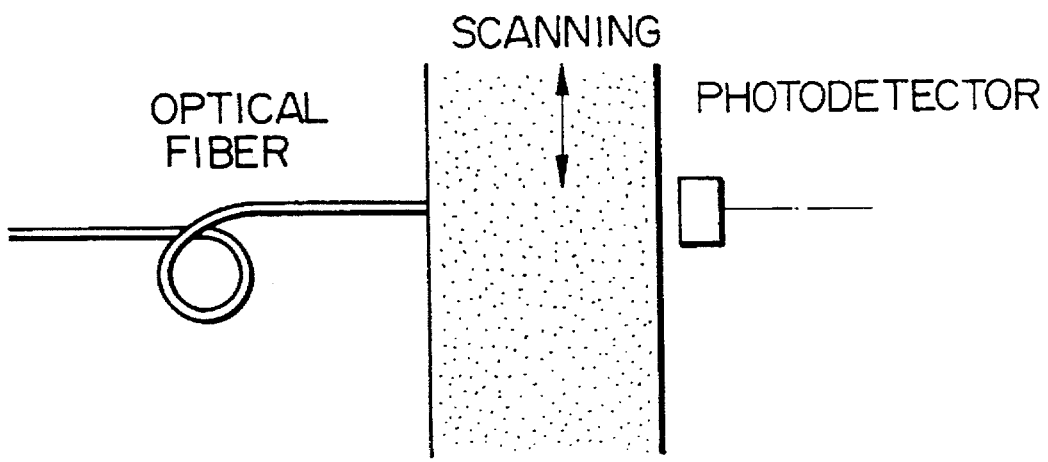
Figure 11:
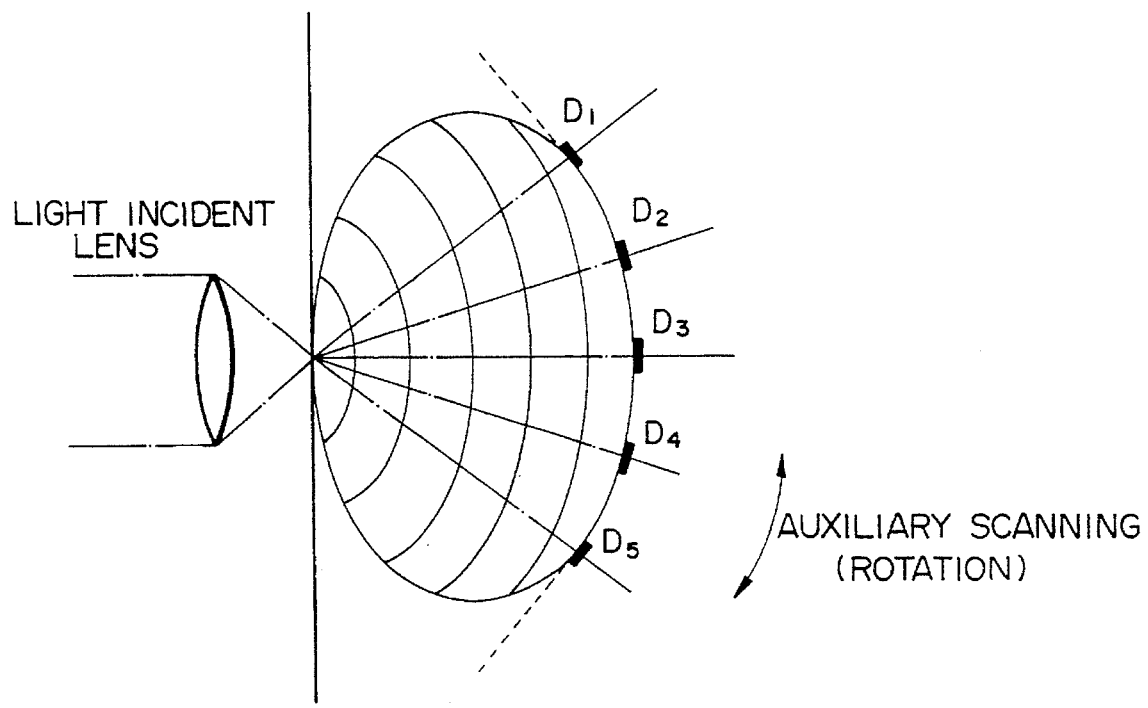
FIG. 11 is a view showing a method utilizing a plurality of photodetectors.

A scanning means for imaging may be constituted by a method of scanning the pair of light source and photodetector (FIG. 10A), a method of moving the scattering medium as the object to be measured (FIG. 10B), or the like. To measure a tomogram, rotary scanning of the scattering medium or the pair of light source and photodetector is required as in X-ray CT. Rotary scanning may be performed simultaneously with translational scanning. In addition, as shown in FIG. 11, a method of causing a plurality of photodetectors $D_1, D_2, \ldots$ to detect a photon density wave concentrically spherically propagating through the scattering medium is also available. This method is used in imaging and measurement of a tomogram. Note that optical information obtained by each photodetector must be normalized in accordance with a distance r between each photodetector and the modulated light incident position.

Generation of the modulated light, selection of a wavelength, modulated light incidence, photodetection, signal extraction, predetermined parameter detection, scanning, and the like described above can be applied when a light source generates various type of repetition pulses.

Arithmetic processing of the degree of saturation of hemoglobin, the concentration of a specific constituent, and other absorption information in a scattering medium, and tomograms thereof is performed at high speed using a computer having a memory, a display, and the like.

4. Detailed Embodiments (1) First Embodiment (Measurement of Absorption Coefficient and the like of Scattering Medium)

Figure 12:
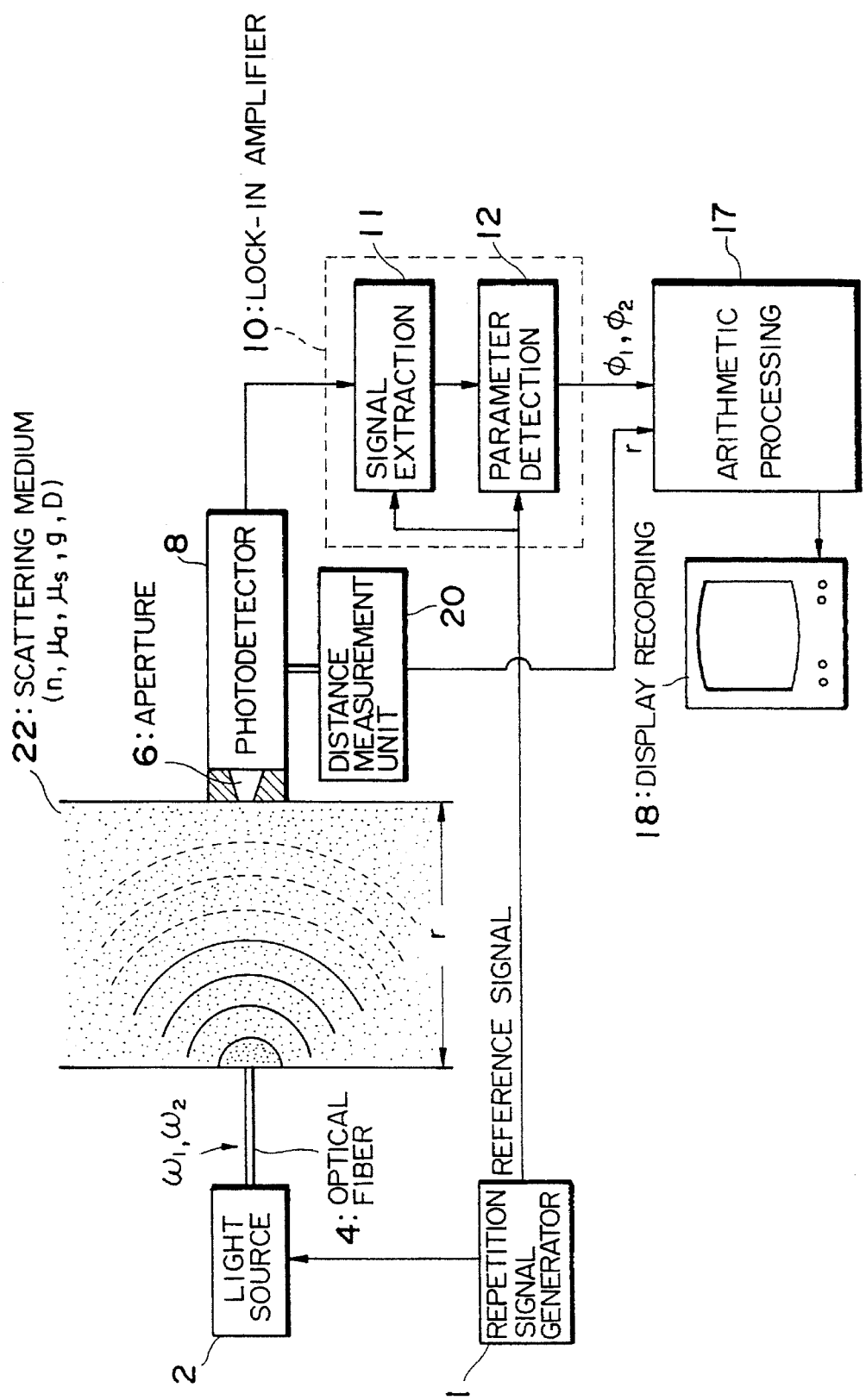
FIG. 12 is a diagram showing an arrangement of the first embodiment.

FIG. 12 shows the first embodiment of the scattering medium optical information measuring apparatus according to the present invention.

A light source 2 utilizing a laser diode generates modulated light $I=I_0(2+M_1\cos\omega_1 t+M_2\cos\omega_2 t)$ (where $I_0$ is a constant, $M_1$ and $M_2$ are the degrees of modulation at angular frequencies $\omega_1$ and $\omega_2$, and t is time) having a predetermined wavelength in accordance with a signal from a repetition signal generator 1.

The wavelength of light from the light source must be appropriately selected in accordance with the type of object to be measured. Light having a wavelength of 700 nm or more generally easily propagate in a living body in relation to absorption of hemoglobin and the like. As shown in FIG. 4, oxyhemoglobin and reduced hemoglobin have different spectral transmittances. If a plurality of wavelengths are used, oxyhemoglobin and reduced hemoglobin can be separately measured.

The resolving power such as imaging in the scattering medium can be increased at higher angular frequencies $\omega_1$ and $\omega_2$ contained in the modulated light, but signal attenuation is undesirably increased. In general, measurement accuracy can be improved when the difference between the angular frequencies $\omega_1$ and $\omega_2$ is increased. It is also preferable to select a frequency which can facilitate the arrangement of a modulated light source, signal extraction in the subsequent stage, predetermined parameter detection, and the like. Three or more different frequencies can be used to further improve the measurement accuracy.

Various types of light sources such as an He-Ne laser can be used in addition to the laser diode. A light source which can facilitate the circuit arrangement for generating modulated light is preferably selected. A light source may generate pulsed light or square photon density wave light. A larger degree of modulation is preferred, but a smaller degree of modulation does not pose any essential problem. The degree of modulation may be determined in favor of the arrangement of the modulation apparatus.

When a laser diode is used as a light source, a drive current can be modulated to easily produce modulated light of about several kHz to 1 GHz. When the frequency exceeds 1 GHz, a laser diode having good frequency characteristics and a high-frequency circuit are required. The modulated light containing the plurality of frequency components can be easily generated by a circuit shown in FIG. 6. The light beams may be generated by different laser diodes and may be synthesized, or the different light beams may be switched along the time axis.

The modulated light from the light source is incident on an object (scattering medium) 22 to be measured serving as a scattering medium through an optical fiber 4. In this case, as described in the previous paragraph, the modulated light may be collimated, and the collimated light may be focused using a condenser lens or pinhole. More specifically, since a diffusion length $l_d=1/(1-g)\mu_s$ is about 3 mm or less in a scattering medium, the incident light is almost perfectly scattered before it propagates straight by about 3 mm, and directivity of incident light is lost. When a scattering medium having a thickness of several mm or more is taken into consideration, a condition for causing the modulated light to be incident as a light spot must be satisfied. As described before, the modulated light may be shaped into a broad beam, the broad beam may be caused to become Incident on the scattering medium and the photodetector may be arranged on the side of the scattering medium opposite to the modulated light incident position along the optical path of this light beam.

A space between the optical fiber 4 and the object (scattering medium) 22 is very small in the embodiment of FIG. 12. However, in practice, this space may be filled with a liquid material or jelly-like material (to be referred to an interface material hereinafter) having almost the same refractive index and scattering coefficient as those of the object 22. That is, the photon density wave having the predetermined frequency component coherently propagates in this interface material and becomes incident on the object, thus posing no problem.

A photodetector 8 has an aperture 6 for controlling an effective area of light-receiving surface. The aperture 6 may be a hole formed on opaque plate. When light is guided to the photodetector through an optical fiber or a light guide, the end face of the optical fiber or the like serves as an effective aperture. In either case, it is preferable to have a structure in which light incident on a portion except the active area of the photodetector is shielded. In addition, the interface medium may be inserted between the photodetection aperture 6 and the object 22. If the modulated light propagating in the scattering medium contains light components having a plurality of wavelengths, a wavelength selection filter (not shown) is inserted between the aperture 6 and the photodetector 8.

Any photodetector such as a phototube, a photodiode, an avalanche photodiode, or a PIN diode can be used as the photodetector 8 in addition to a photomultiplier. Any photodetector can be selected if it has spectral sensitivity characteristics and frequency characteristics enough to detect the modulated light having the predetermined frequency component of the light having the predetermined wavelength. If output light is weak, a high-sensitivity photodetector is used.

An output signal from the photodetector is input to a lock-in amplifier 10. The lock-in amplifier 10 accurately extracts waves having predetermined frequency components (in this case, the waves having the angular frequencies $\omega_1$ and $\omega_2$) from a photodetection signal. The extracted waves are compared with the reference signal from the repetition signal generator 1 to detect a phase difference and an amplitude which serve as predetermined parameters corresponding to these waves. In FIG. 12, a function of extracting the signal having the predetermined frequency component is represented as signal extraction 11, and a function of detecting the predetermined parameters is represented as parameter detection 12.

Figure 13:
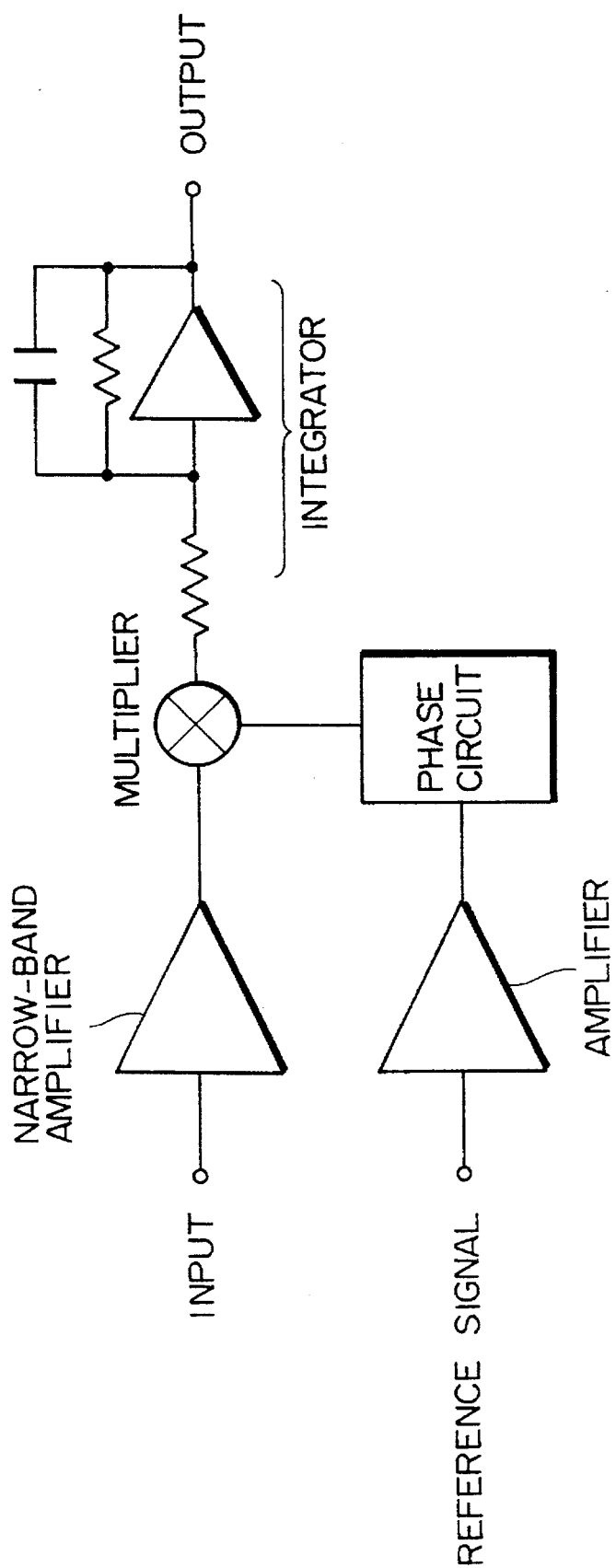
FIG. 13 is a diagram showing the arrangement of the main part of a lock-in amplifier.

FIG. 13 shows an arrangement of the main part of this lock-in amplifier. The lock-in amplifier can precisely select and detect only a component having the same frequency as and a predetermined phase relationship with a reference signal from a small repeated signal mixed in noise. The weak input signal is amplified with a narrow band, and the amplified signal is multiplied with the reference signal or synchronously rectified (also called phase sensitive detection), and an integration value thereof is output. Any reference signal can be used if it is synchronized with the input signal to be measured. In this embodiment, the output signal from the repetition signal generator 1 is used, but a signal obtained upon reception of the modulated light on another photodetector may be used as the reference signal.

Figure 14:
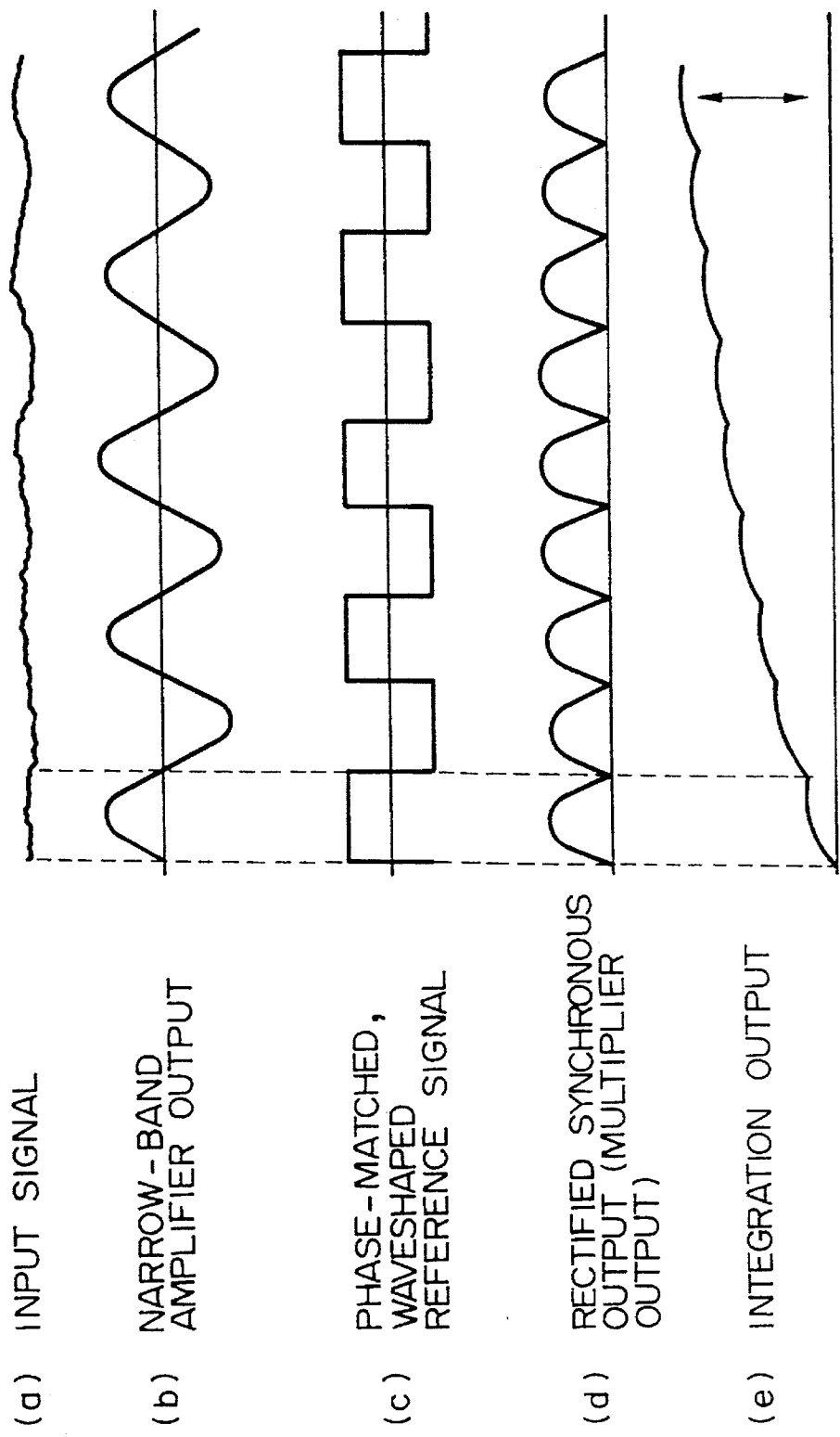
FIG. 14 is a chart showing waveforms of the respective components in the lock-in amplifier.

The waveforms of the respective signals in this lock-in amplifier are shown in FIG. 14. FIG. 14(a) shows an input signal, FIG. 14(b) shows an output from the narrow-band amplifier, FIG. 14(c) shows an output from a phase circuit, FIG. 14(d) shows an output from the multiplier or a synchronously detected output, and FIG. 14(e) shows an output from the integrator. The signal-to-noise ratio (S/N ratio) of the detection system using the lock-in amplifier is determined by an equivalent noise bandwidth $\Delta f$ of the system and is in inverse proportion to $(\Delta f)^{1/2}$.

Figure 15:
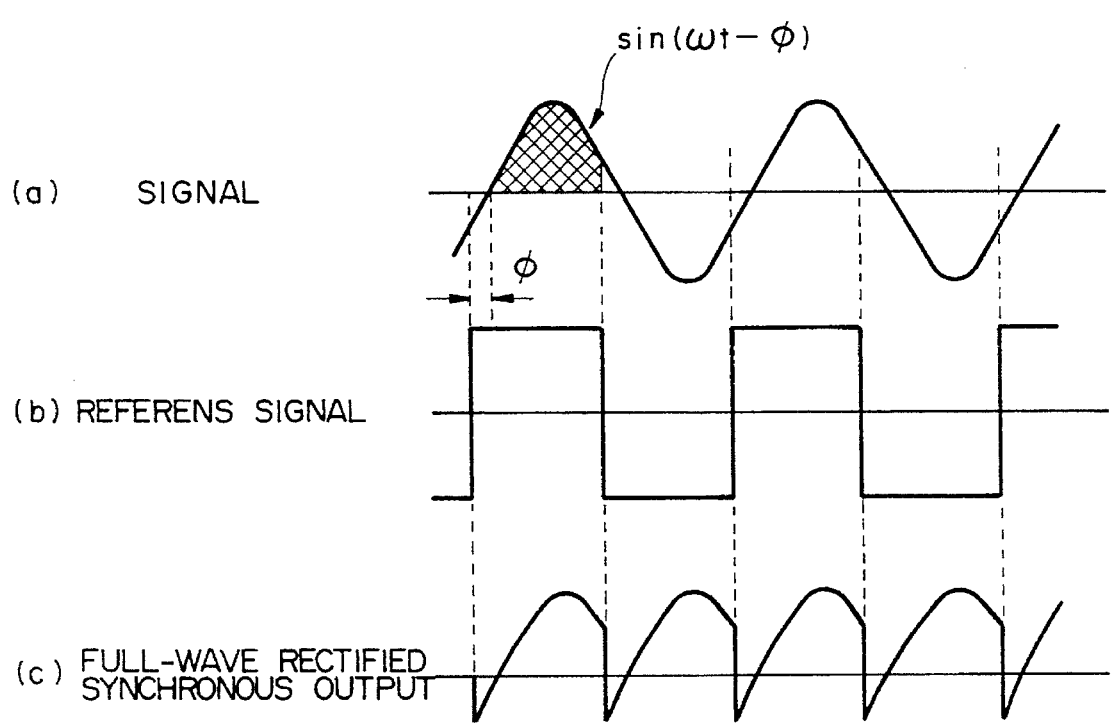
FIG. 15 is a chart showing a phase shift.

In this lock-in amplifier, as shown in FIG. 15, an output corresponding to a signal $\sin(\omega t - \Phi)$ (FIG. 15(a)), which is phase-delayed by $\Phi$ from the reference signal (FIG. 15(b)) is $A\cos\Phi$. An average value of the synchronously detected output becomes maximum when $\Phi=0$. Note that A is a constant. Therefore, by sifting the phase of the reference signal from the phase circuit shown in FIG. 13, the phase of the input signal (FIG. 14(a)) to the lock-in amplifier can be known from a shift amount of the phase of the reference signal which maximizes the synchronously rectified output, i.e., when $\Phi=0$.

Figure 9C:
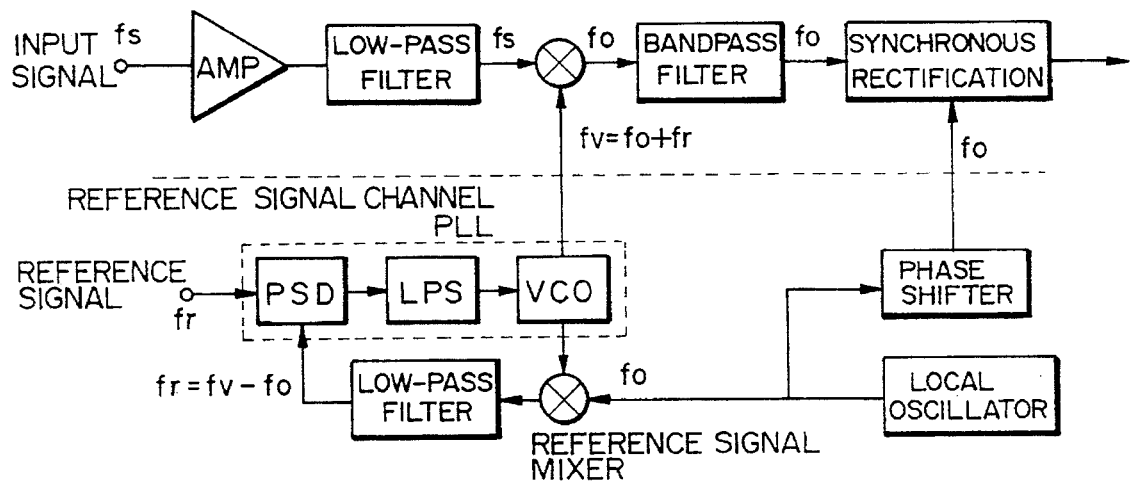

A commercially available lock-in amplifier responds up to several MHz. In a lock-in amplifier of several MHz to 1 GHz, the operational principle is the same as that of the above commercially available lock-in amplifier, but must be arranged using a high-speed electronic device. In the region of several MHz to 1 GHz, a heterodyne amplifier is generally connected to the input to the narrow-band amplifier in FIG. 13. This lock-in amplifier is called a heterodyne type lock-in amplifier. The arrangement of this heterodyne type lock-in amplifier is illustrated in FIG. 9C. The heterodyne amplifier has a function of converting the input signal into a signal representing a difference between the frequency of the input signal and the oscillation frequency of a local oscillator. This difference signal, i.e., a signal having an intermediate frequency of several MHz or less is input to the lock-in amplifier described above. In this case, the reference signal is a signal synchronized with the intermediate frequency.

A conventional commercially available lock-in amplifier outputs an amplitude $I_p$ of the signal of the predetermined frequency extracted from the photodetection signal from the photodetector 8, an amplitude obtained upon separation into two orthogonal components, or a phase difference $\Phi$ between the input signal and the reference signal. A function of generating this output is included in parameter detection 12 in the lock-in amplifier 10 in FIG. 12.

In this embodiment, of all the parameters described above, the phase difference between the input signal and the reference signal is used. When a phase difference $\Phi$ in which an offset component such as a phase delay generated in a modulated light incident optical fiber or the like is corrected is used, this phase difference $\Phi$ corresponds to the phase delay of the photon density wave having the predetermined frequency component and propagating in the scattering medium as the object to be measured, i.e., the phase difference $\Phi$ in equation (1.8). This offset component is determined by the arrangement of the apparatus and serves as a constant. The offset component may be actually measured. In this manner, the phase differences $\Phi_1$ and $\Phi_2$ corresponding to the two predetermined frequencies $\omega_1$ and $\omega_2$ are obtained and correspond to the phase differences $\Phi_1$ and $\Phi_2$ calculated in equation (1.14), respectively.

An arithmetic processing means 17 in FIG. 12 calculates the absorption coefficient $\mu_a$ of the scattering medium as the object to be measured, using the resultant $\Phi_1$ and $\Phi_2$. More specifically, the absorption coefficient $\mu_a$ is obtained using equation (1.14) or the like. This operation can be easily performed at high speed by a microcomputer incorporated in the arithmetic processing means. Optical information such as the equivalent scattering coefficient $\mu_s'$ of the scattering medium as the object can be calculated using the resultant $\mu_a$ value, and optical information such as the concentration of the absorptive constituent can also be calculated using the spectral absorbance of the specific absorptive constituent, as needed. If a scattering medium contains a plurality of absorptive constituents, modulated light having a plurality of wavelengths is used, as previously described. In this case, a method using modulated light containing light components having a plurality of different wavelengths or a method of measuring optical information for the plurality of different wavelengths in a time division manner may be used, as described earlier. A distance r between the incident position of the modulated light incident on the scattering medium as the object and the photodetection position is measured using a distance measuring unit 20 in FIG. 12, and the measurement is normalized using the value r, thereby obtaining an absorption coefficient per unit distance, a concentration per unit distance, and the like.

When measurement of various pieces of optical information is performed at a different time, e.g., $t_1$ after the above measurement while the arrangement remains the same, changes in these pieces of optical information over time can be measured. The arithmetic processing means 17 has a function of storing optical information values thus obtained, and a display recording means 18 in FIG. 12 displays or records the information.

In the embodiment shown in FIG. 12, a pair of modulated light incident position and photodetection position can be scanned or moved (not shown) with respect to the scattering medium 22 as the object to be measured. In this case, measurements of the various pieces of optical information are performed at different times and different locations. If the distance r remains the same in the measurements at different locations, and the scattering medium (object) 22 is set in a steady state, the spatial distribution of the optical information can be measured. When the distance r varies depending on different locations, optical information normalized by the distance r values as outputs from the distance measuring unit 20 is used.

(2) Second Embodiment (Tomographic Measuring Apparatus)

Figure 16:
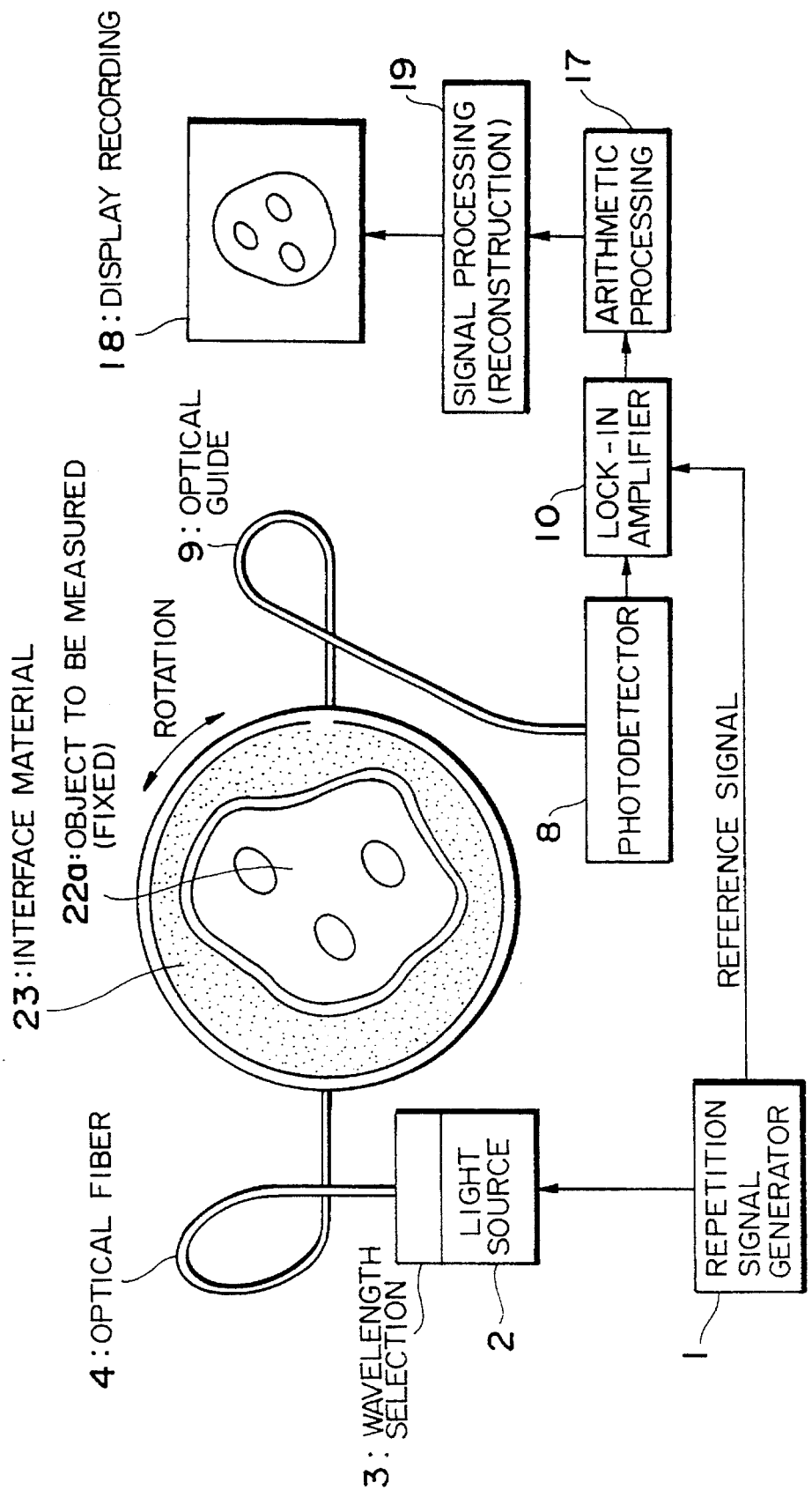
FIG. 16 is a diagram showing an arrangement of the second embodiment.

FIG. 16 is a view showing an arrangement of an apparatus of the second embodiment to explain tomographic measurement of a scattering medium. In the first embodiment, light constituting a photon density wave having a predetermined frequency component is detected in a predetermined direction of optical axis, and various types of optical information contained in a spindle-shaped portion in the scattering medium along the optical axis are measured. However, in the second embodiment, an object 22a to be measured or a pair of modulated light incident position and photodetection position are rotated and scanned with respect to a scattering medium as an object 22a to be measured so that the direction of optical axis becomes each of all directions. Using various types of optical information obtained as in the first embodiment, a tomogram is reconstructed as in X-ray CT (Computer Tomography).

The basic arrangement shown in FIG. 16 is substantially the same as that of FIG. 12, except for a portion for holding the object 22a, a wavelength selecting means 3, a light guide 9, a tomographic reconstruction signal processing means 19, and the like.

A light source 2 generates modulated light $I=I_0(2+M_1\cos\omega_1 t+M_2\cos\omega_2 t)$ of light having a predetermined wavelength in accordance with a signal from a repetition signal generator 1. The desired wavelength of the modulated light from the light source is selected by the wavelength selecting means 3, and the modulated light having the selected wavelength is incident, through an optical fiber 4, on an object 22a to be measured surrounded by an interface material 23. The interface material 23 has the optical characteristics described above and is surrounded by a thin-film vessel having a low reflectance. Light incident on the vessel containing the interface material is hardly reflected on the interface between the vessel and the interface material. If the outer and inner surfaces of the thin film are rough surfaces, the incident light has light components which propagate in all directions. With this arrangement, the modulated photon density wave propagates through the interface material and the object 22a and reaches a photodetection point located on the opposite side. The light guide 9 is located at the photodetection point, and it is coupled to the photodetector 8, so that the light is incident on the photodetector 8 through this light guide. The interior of the vessel containing the interface material except for a portion around an opening of the light guide and a portion around a light incident aperture is preferably constituted by an absorption medium with respect to light. Therefore, light reflection on the inner surface can be eliminated, and accurate measurements can be performed.

Figure 17:
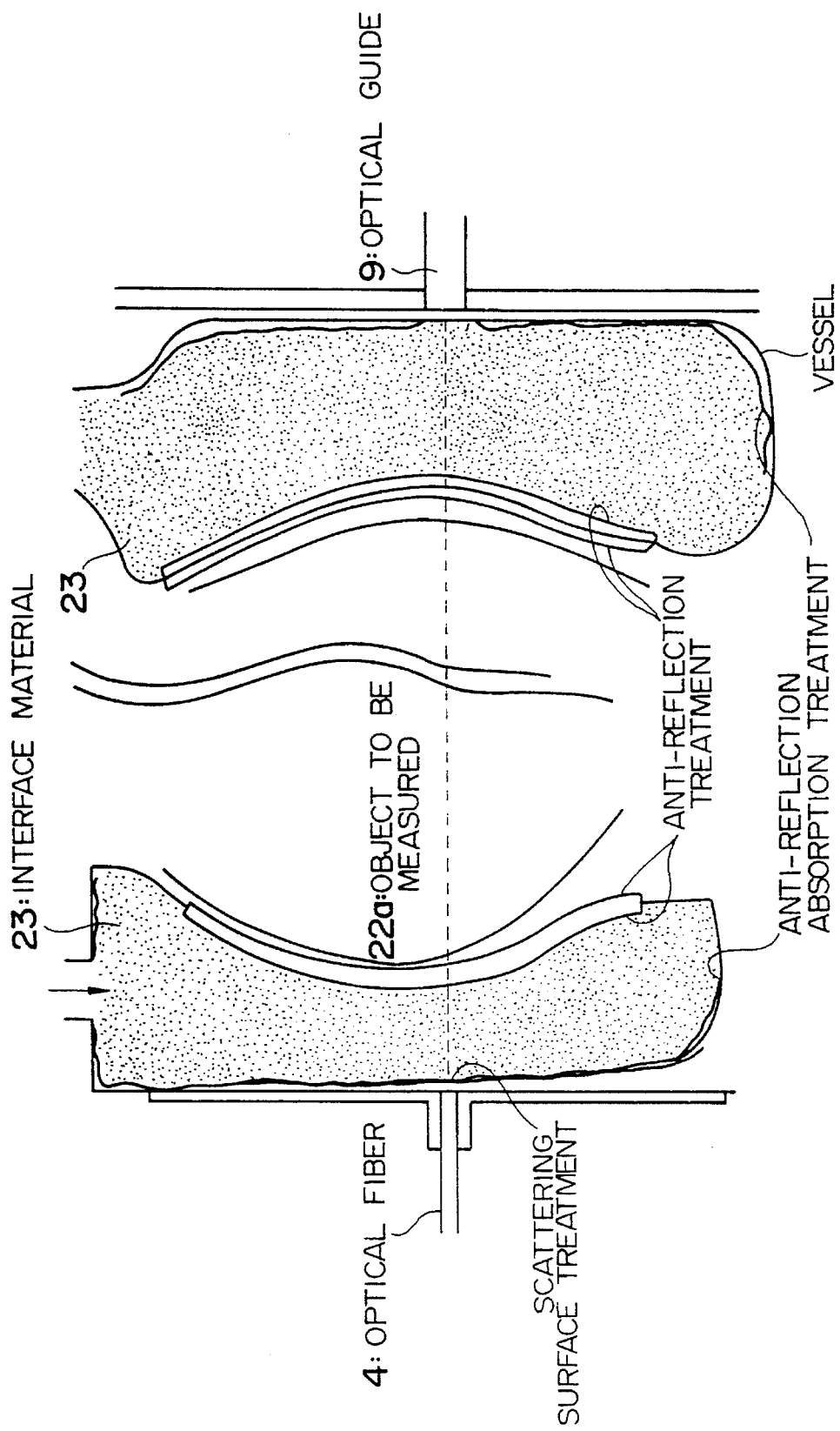
FIG. 17 is a view showing two interface vessels.

The object 22a is rotated relative to the light source optical fiber 4, the photodetection light guide 9, the interface material 23, and the vessel. The vessel must have a structure that although the interface vessel has a circular outer cross-section, the interior of the vessel conforms to the shape of object 22a to be measured, and no gap is formed even if the object 22a is rotated. This structure can be achieved by a method of preparing one vessel which surrounds the object 22a, as shown in FIG. 16, or a method of preparing two vessels respectively on the light incident and exit sides as shown in FIG. 17. In either case, the interface material must be brought into tight contact with the light incident and photodetection apertures, and at the same time, the inner side of the interface material can be brought into contact with the object 22a to be measured by utilizing the gravity or a pressure.

An optical signal obtained as described above is processed in the same manner as in the first embodiment to obtain optical information corresponding to optical axes of all directions of the object 22a. Therefore, image reconstruction as in X-ray CT can be performed by a signal processing means 19, and a tomogram can be obtained by an image display recording means 18. Even if the object 22a to be measured is rotated, and other members are kept stationary in the arrangement of FIG. 16, the same measurement as described above can be performed.

The tomograms obtained in this embodiment represent an absorption coefficient distribution, a scattering coefficient distribution, a concentration distribution of a specific constituent, and a distribution of the degree of saturation of oxyhemoglobin all in a scattering medium.

(3) Third Embodiment (Utilization of a Plurality of Photodetectors)

A plurality of photodetectors are used in the third embodiment. Equations (1.1) to (1.4) are established in all directions within a scattering medium. For this reason, a plurality of photodetectors can be used, as shown in FIG. 11. With this arrangement, the distribution of optical information of the scattering medium like a panoramic image is obtained by viewing an object from the light incident point in a wide range. In this case, the plurality of photodetectors can be arranged on the outer surface of the scattering medium at arbitrary positions. This arrangement makes it possible to shorten the measurement time as compared with a scheme in which one photodetector is moved from $D_1$ to $D_5$. When the pitch between the adjacent photodetectors is large, the photodetector array may be rotated and scanned about the light incident point to obtain an image having a higher sampling density. In this case, the interface material as shown in the second embodiment may be used, and measurements of objects having different distances depending on the directions can be performed.

End faces of a plurality of optical fibers having the same length may be located at the positions of the photodetectors, and opposite ends of the optical fibers may be connected to the plurality of photodetectors or the photodetector array. If the distances r are different from each other, the distance r is preferably measured by another method, and the various types of optical information are preferably normalized with the resultant values r. The interface medium shown in the second embodiment may be utilized.

(4) Fourth Embodiment (CT Using a Plurality of Photodetectors)

The fourth embodiment is obtained by adding the arrangement of the third embodiment to the tomographic measuring apparatus of the second embodiment. The arrangement of the fourth embodiment can be similar to a fan beam scheme in X-ray CT to obtain a tomogram at high speed.

As has been described above, according to an apparatus for measuring optical information of a scattering medium, and a method therefor of the present invention, the influence of a scattering constituent can be separated from the influence of an absorptive constituent, and accurate measurements can be performed. Optical information such as an equivalent scattering coefficient, an absorption coefficient, and the concentration of a specific constituent, spatial distributions thereof, changes in these pieces of optical information over time, and distributions thereof within a slice can be measured. In the optical information measuring apparatus using the present invention, use of modulated light can improve light utilization efficiency, and measurement accuracy can be substantially improved by the principle of detecting parameters such as a phase corresponding to a photon density wave propagating in the scattering medium. For these reasons, measurement, imaging, tomographic measurement, and the like of the above optical information of a human head, a human trunk, and a plant such as a tree can be performed. Therefore, the present invention is a remarkable invention capable of performing optical measurement of optical information such as the equivalent scattering coefficient, the absorption coefficient, and the concentration of a specific constituent of a scattering medium, imaging thereof, and tomographic measurement thereof. The present invention has great academic, industrial, and social influences and effects.

What is claimed is:

1. An apparatus for measuring optical information in a scattering medium containing an absorptive constituent, comprising:

light-emitting means for emitting modulated light having a single predetermined light wavelength and at least two predetermined modulation frequency components;

light-incident means for causing said modulated light to be incident on the scattering medium;

photodetecting means for photodetecting the modulated light which has been changed during propagation in the scattering medium, through an aperture located near an outer surface of the scattering medium;

signal extracting means for extracting signals of said predetermined modulation frequency components constituting the modulated light from signals photodetected by said photodetecting means;

parameter detecting means for comparing said signals extracted by said signal extracting means with reference signals of said predetermined modulation frequency components of the modulated light to be incident on the scattering medium, respectively, and detecting predetermined parameters respectively corresponding to said signals having the predetermined modulation frequency components, said parameters being associated with propagation of said modulated light in the scattering medium and scattering and absorption of said modulated light in the scattering medium; and arithmetic processing means for calculating an absorption coefficient of the scattering medium by use of said parameters detected by the parameter detecting means, in accordance with a given relationship between the predetermined parameters and the scattering and absorption for said modulated light during propagation in the scattering medium.

2. An apparatus for measuring optical information in a scattering medium according to claim 1, wherein said arithmetic processing means further comprises means for arithmetically calculating an equivalent scattering coefficient of the scattering medium by use of said absorption coefficient.

3. An apparatus for measuring optical information in a scattering medium according to claim 1, wherein said predetermined parameter includes a phase difference ($\Phi$); and said given relationship is represented by the following formula:

$$\Phi^2 = 3(\mu_a + (1-g)\mu_s)\left(\frac{r^2}{2v}\right) \times ((\omega^2 + (v\mu_a)^2)^{1/2} - v\mu_a)$$

wherein $\Phi$ is the phase difference, $\mu_a$ is an absorption coefficient, g is an average value of $\cos\theta$ with respect to a scattering angle $\Theta$, $\mu_s$ is a scattering coefficient, r is a distance between a modulated light incident point and a photodetection point, v is a speed of light in the scattering medium, and $\omega$ is the modulation angular frequency of the modulated light.

4. An apparatus for measuring optical information in a scattering medium according to claim 1, said predetermined parameter includes an amplitude ($I_p$); and said given relationship is represented by the following formula:

$$\left(\ln\left(\frac{SvM}{4\pi\alpha r I_p}\right)\right)^2 = $$

$$3(\mu_a + (1-g)\mu_s)\left(\frac{r^2}{2v}\right) \times ((\omega^2 + (v\mu_a)^2)^{1/2} + v\mu_a)$$

wherein S is a number of incident photons generated by a light source, v is a speed of light in the scattering medium, M is a degree of modulation of the modulated light, $\alpha$ is a photon diffusion constant, r is a distance between a modulated light incident point and a photodetection point, $I_p$ is the amplitude, $\mu_a$ is an absorption coefficient, g is an average value of $\cos\theta$ with respect to a scattering angle $\Theta$, $\mu_s$ is a scattering coefficient, and $\omega$ is the modulation angular frequency of the modulated light.

5. An apparatus for measuring optical information in a scattering medium according to claim 1, further comprising scanning means for scanning the scattering medium with the modulated light incident from said light-incident means, and arithmetic display means for arithmetically processing a position signal corresponding to scanning by said scanning means and the optical information obtained by said arithmetic processing means and visually displaying the processed position signal.

6. An apparatus for measuring optical information in a scattering medium according to claim 1, further comprising displacing means for displacing an incident position of the modulated light from said light-incident means on the scattering medium along a slice of the scattering medium, and image reconstructing means for reconstructing a tomogram of the scattering medium on the basis of a displacement signal corresponding to a displacement by said displacing means and the optical information obtained by said arithmetic processing means.

7. An apparatus for measuring optical information in a scattering medium according to claim 1, wherein said photodetecting means comprises a plurality of photodetectors for independently detecting the modulated light components propagating through the scattering medium.

8. An apparatus for measuring optical information in a scattering medium according to claim 1, wherein the predetermined parameter includes a phase difference.

9. An apparatus for measuring optical information in a scattering medium according to claim 1, wherein the predetermined parameter includes an amplitude.

10. An apparatus for measuring optical information in a scattering medium according to claim 1, wherein said arithmetic processing means further comprises means for arithmetically calculating a concentration of the absorptive constituent in the scattering medium by use of said absorption coefficient.

11. An apparatus for measuring optical information in a scattering medium according to claim 1, wherein the scattering medium contains at least two absorptive constituents;

the light-emitting means emits at least two modulated lights each of which has a single predetermined light wavelength and at least two predetermined modulation frequency components, said light wavelengths of the modulated lights being different from each other in absorption coefficients with respect to the absorptive constituents in the scattering medium;

the light-incident means causes each of said modulated lights to be incident on the scattering medium;

the photodetecting means photodetects each of the modulated lights which has been changed during propagation in the scattering medium;

the signal extracting means extracts signals of said predetermined modulation frequency components constituting each of the modulated lights;

the parameter detecting means compares said signals with reference signals of said predetermined modulation frequency components of each of the modulated lights to be incident on the scattering medium, respectively, and detects predetermined parameters respectively corresponding to said signals; and the arithmetic processing means calculates an absorption coefficient of the scattering medium for each of said modulated lights by use of said parameters detected by the parameter detecting means, in accordance with a given relationship between the predetermined parameters and the scattering and absorption for each of said modulated lights during propagation in the scattering medium, and calculates a concentration of each of the absorptive constituents in the scattering medium by use of said absorption coefficients.

12. A method of measuring optical information in a scattering medium containing an absorptive constituent, comprising:

emitting modulated light having a single predetermined light wavelength and at least two predetermined modulation frequency components;

causing said modulated light to be incident on the scattering medium;

photodetecting the modulated light which has been changed during the propagation in the scattering medium, through an aperture located near an outer surface of the scattering medium;

extracting signals of said predetermined modulation frequency components constituting the modulated light from signals photodetected in the photodetecting step;

comparing said signals extracted in the extracting step with reference signals of said predetermined modulation frequency components of the modulated light to be incident on the scattering medium, respectively, and detecting predetermined parameters respectively corresponding to said signals having the predetermined modulation frequency components, said parameters being associated with propagation of said modulated light in the scattering medium and scattering and absorption of said modulated light in the scattering medium; and calculating an absorption coefficient of the scattering medium by use of said parameters detected in the comparing step, in accordance with a given relationship between the predetermined parameters and the scattering and absorption for said modulated light during propagation in the scattering medium.

13. A method of measuring optical information in a scattering medium according to claim 12, further comprising calculating an equivalent scattering coefficient of the scattering medium by use of said absorption coefficient obtained in the step of calculating an absorption coefficient.

14. A method of measuring optical information in a scattering medium according to claim 12, wherein the predetermined parameter obtained in the comparing step includes a phase difference.

15. A method of measuring optical information in a scattering medium according to claim 12, further comprising a step of calculating a concentration of the absorptive constituent in the scattering medium by use of said absorption coefficient obtained in the sixth step.

16. A method of measuring optical information in a scattering medium according to claim 12, wherein the scattering medium contains at least two absorptive constituents;

in the emitting step, at least two modulated lights each of which has single predetermined light wavelength and at least two predetermined modulation frequency components are emitted, said light wavelengths of the modulated lights being different from each other in absorption coefficients with respect to the absorptive constituents in the scattering medium;

in the causing step, each of said modulated lights is entered on the scattering medium;

in the photodetecting step, each of the modulated lights which have been changed during propagation in the scattering medium is photodetected;

in the extracting step, signals of said predetermined modulation frequency components constituting each of the modulated lights are extracted;

in the comparing step, said signals are compared with reference signals of said predetermined modulation frequency components of each of the modulated lights to be incident on the scattering medium, respectively, and predetermined parameters respectively corresponding to said signals are detected; and in the calculating step, an absorption coefficient of the scattering medium for each of said modulated lights is calculated by use of said parameters detected in the fifth step, in accordance with a given relationship between the predetermined parameters and the scattering and absorption for each of said modulated lights during propagation in the scattering medium, and a concentration of each of the absorptive constituents in the scattering medium is calculated by use of said absorption coefficients.

17. A method of measuring optical information in a scattering medium according to claim 12, wherein the predetermined parameter includes a phase difference.

18. A method of measuring optical information in a scattering medium according to claim 12, wherein said predetermined parameter includes a phase difference ($\Phi$); and said given relationship is represented by the following formula:

$$\Phi^2 = 3(\mu_a + (1-g)\mu_s)\left(\frac{r^2}{2v}\right) \times ((\omega^2 + (v\mu_a)^2)^{1/2} - v\mu_a)$$

wherein $\Phi$ is the phase difference, $\mu_a$ is an absorption coefficient, g is an average value of $\cos\Theta$ with respect to a scattering angle $\Theta$, $\mu_s$ is a scattering coefficient, r is a distance between a modulated light incident point and a photodetection point, v is a speed of light in the scattering medium, and $\omega$ is the modulation angular frequency of the modulated light.

19. A method of measuring optical information in a scattering medium according to claim 12, wherein said predetermined parameter includes an amplitude ($I_p$); and said given relationship is represented by the following formula:

$$\left(\ln\left(\frac{SvM}{4\pi\alpha r I_p}\right)\right)^2 = 3(\mu_a + (1-g)\mu_s)\left(\frac{r^2}{2v}\right) \times ((\omega^2 + (v\mu_a)^2)^{1/2} + v\mu_a)$$

wherein S is a number of incident photons generated by a light source, v is a speed of light in the scattering medium, M is a degree of modulation of the modulated light, $\alpha$ is a photon diffusion constant, r is a distance between a modulated light incident point and a photodetection point, $I_p$ is the amplitude, $\mu_a$ is an absorption coefficient, g is an average value of $\cos\Theta$ with respect to a scattering angle $\Theta$, $\mu_s$ is a scattering coefficient, and $\omega$ is the modulation angular frequency of the modulated light.

* * * * *